United States Patent [19]
Kumar et al.

[11] Patent Number: 6,160,376
[45] Date of Patent: Dec. 12, 2000

[54] BATTERY CHARGER CAPABLE OF EVALUATING BATTERY CHARGE STATE

[75] Inventors: Yashdeep Kumar, Kalamazoo; Donald Malackowski, Schoolcraft, both of Mich.

[73] Assignee: Stryker Corporation, Kalamazoo, Mich.

[21] Appl. No.: 09/455,091

[22] Filed: Dec. 6, 1999

Related U.S. Application Data

[62] Division of application No. 09/102,142, Jun. 22, 1998, Pat. No. 6,018,227.

[51] Int. Cl.$^7$ ........................ H01M 10/44; H01M 10/46
[52] U.S. Cl. ............................................ 320/116; 320/734
[58] Field of Search ................................... 320/116, 119, 320/134, 150, 152, 160, 162

[56] References Cited

U.S. PATENT DOCUMENTS

| | | |
|---|---|---|
| 3,911,351 | 10/1975 | Saslow . |
| 4,288,733 | 9/1981 | Bilanceri et al. . |
| 4,644,245 | 2/1987 | Brown . |
| 4,878,007 | 10/1989 | Gábor et al. . |
| 5,045,769 | 9/1991 | Everett, Jr. . |
| 5,136,231 | 8/1992 | Faulk . |
| 5,182,509 | 1/1993 | Simmonds . |
| 5,187,422 | 2/1993 | Izenbaard et al. . |
| 5,229,705 | 7/1993 | Kato . |
| 5,280,230 | 1/1994 | Mahoney . |
| 5,489,836 | 2/1996 | Yuen . |
| 5,534,765 | 7/1996 | Kreisinger et al. . |
| 5,541,496 | 7/1996 | Simmonds . |
| 5,557,188 | 9/1996 | Piercey . |
| 5,582,928 | 12/1996 | Farley . |
| 5,592,069 | 1/1997 | Dias et al. . |
| 5,694,024 | 12/1997 | Dias et al. . |

FOREIGN PATENT DOCUMENTS

| | | |
|---|---|---|
| 0 147 241 | 7/1985 | European Pat. Off. . |
| 0 255 631 | 2/1988 | European Pat. Off. . |
| 0 399 821 | 11/1990 | European Pat. Off. . |
| 0 480 648B1 | 4/1992 | European Pat. Off. . |

OTHER PUBLICATIONS

Dallas Semiconductor, DS2434—Battery Identification Chip, Preliminary Specification sheet, Dec., 1995.

*Primary Examiner*—Edward H. Tso
*Attorney, Agent, or Firm*—Flynn, Thiel, Boutell & Tanis, P.C.

[57] ABSTRACT

A battery charger (20) for charging batteries that evaluates the post-charge state of the batteries. A load resistor (70) and a temperature sensor (286) are associated with each battery. After the charging of the battery, a processor (124) receives signals indicating the voltage-at-load of the battery when it is connected to the load resistor and the battery temperature. A memory (282) internal to the battery stores historical voltage-at-load data for the battery. The processor based, the voltage-at-load, the battery temperature and the historical voltage-at-load data for the battery determines an average voltage-at-load for the battery. Based on the average voltage-at-load and data specific to that battery, the processor determines the charge state of the battery. Data representative of the charge state is presented on a display (30) integral with the charger. Data useful for determining both the average voltage-at-load and the charge state for the battery are found in a memory (70) in a module that is removably attached to the charger or in the battery memory (282).

34 Claims, 19 Drawing Sheets

BATTERY CHARGER CAPABLE OF EVALUATING BATTERY CHARGE STATE

This is a division of Ser. No. 09/102,142, filed Jun 22, 1998, now U.S. Pat. No. 6,018,227.

FIELD OF THE INVENTION

This invention relates generally to battery chargers used to charge sterilizable battery packs such as battery packs that are used to power medical instruments. More particularly, this invention relates to a charger configured to charge different rechargeable batteries to which different charging currents are applied. This invention also relates to a charger and complementary battery pack that, collectively, provide information about the charge state and sterilization history of the battery pack.

BACKGROUND OF THE INVENTION

Over the past few years, the cordless, battery operated powered surgical tool has become a very popular tool for use in surgery. As the name implies, this type of tool is provided with a battery that serves as the power source for the energy-consuming component integral with the tool. Typically, this component is an electrically driven motor. The integration of the battery into the tool eliminates the need to provide the tool with a power cord that is connected to an external power source. The elimination of the power cord offers several benefits over corded surgical tools. Surgical personnel using this type of tool do not have to concern themselves with either sterilizing a cord so that it can be brought into the sterile surgical field surrounding the patient or ensuring that, during surgery, an unsterilized cord is not inadvertently introduced into the surgical field. Moreover, the elimination of the cord results in the like elimination of the physical clutter and field-of-view blockage the cord otherwise brings to a surgical procedure.

An integral part of any battery-powered tool is, naturally, the battery. Most battery-powered surgical tools are designed to be used with rechargeable batteries. These rechargeable batteries, like other rechargeable batteries, typically are formed from one or more NiCd cells. Once a battery is discharged, it is coupled to a complementary charger. The charger applies a current to the battery's cells to store energy in the cells.

Unlike other rechargeable batteries, a rechargeable battery intended for use with a surgical tool must be sterilizable so that it can be placed in close proximity to the open surgical site on a patient. Often, these batteries are sterilized by placing them in an autoclave wherein the temperature is approximately 270° F., the humidity is approximately 100% and the atmospheric pressure approximately 30 psi. The repetitive exposure to this environment causes a battery cells' ability to store electric charge to degrade.

Modern battery chargers, especially those that are used to charge sterilizable batteries, do more than simply apply currents to the batteries with which they are used. Often, a battery charger includes a circuit for measuring the voltage across a battery as it is being charged. A charging circuit, in turn, applies a selected current to the battery based on the voltage across the battery. Many chargers also include a load resistor that is selectively connected across the battery. Once the battery charging cycle has been completed, this resistor is connected across the battery and the voltage across it is measured. This voltage measurement is used to determine the state of the cells integral with the battery. This measure of cell state is, in turn, used as measure of the utility of a battery. For example, if, due to sterilization-induced degradation, the cells of a battery can no longer hold a charge, the voltage over the load resistor will be relatively low. If the load resistor voltage is below a select value, some chargers are configured to generate a display that indicates that the battery's current-storage capabilities have decayed to the point where the battery should be replaced.

While present battery chargers have proven to be useful devices, they are not without some limitations. It has been found that a voltage across a load resistor only provides a relatively inaccurate measure of the charge stored with a set of battery cells. Also, as the charge-storing capacity of a sterilizable battery decreases, present chargers do not offer any indication if such decrease is within a normal range.

Furthermore, present battery chargers are only designed to be used with one particular type of battery. There are two reasons for this. First, most battery chargers are provided with sockets designed to receive batteries having a specifically shaped head. Secondly, most battery charges are merely provided with components that are configured to deliver charge to one type of battery. Specifically, the internal circuitry of a typical charger is configured to deliver a select set of currents in response to a select set of battery voltage measurements. Consequently, each time a facility purchases a product that employs a new type of rechargeable battery, it is also required to purchase the charger that goes with the battery. The need to make this extra charger purchase, in addition to increasing the overall cost of the product purchase, requires the facility to store and maintain one additional piece of equipment.

SUMMARY OF THE INVENTION

This invention relates to an improved battery charger and a battery that is especially adapted for use with the charger. More particularly, the battery charger of this invention provides suitable charging currents, in proper sequence, to different batteries even if those batteries require different charging currents. When this battery charger is used with a complementary battery especially designed for use with the charger, the charger provides both relatively accurate data regarding the post-charging charge stored in the battery as well as indication of whether the battery's ability to store charge is within an expected range.

BRIEF DESCRIPTION OF THE DRAWINGS

This invention is pointed out with particularity in the claims. The above and further features of the invention may be better understood by reference to the following description taken in conjunction with the accompanying drawings, in which:

DETAILED DESCRIPTION

Figure 1:
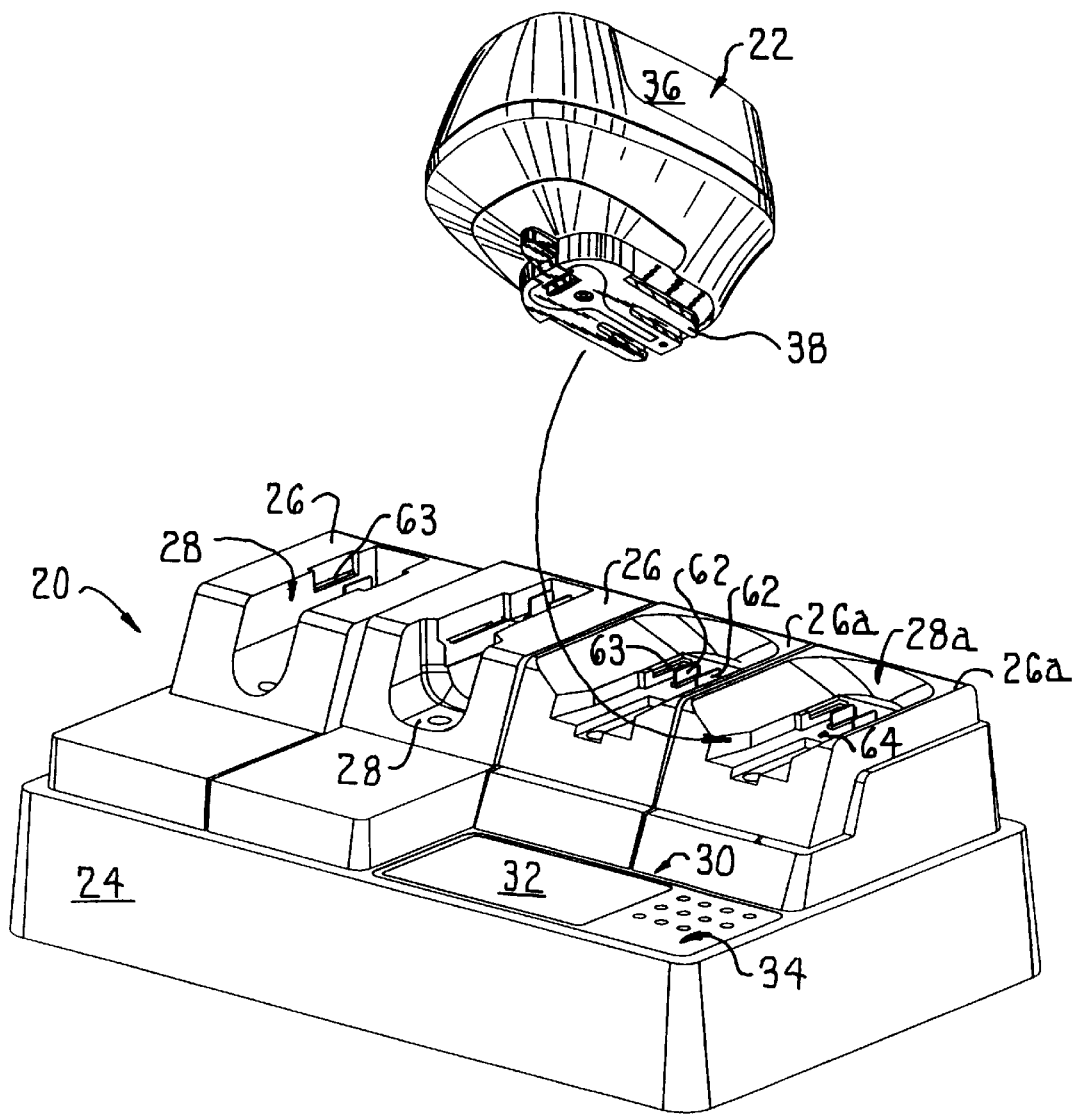
FIG. 1 is a perspective view of a battery charger of this invention and of a complementary battery with which the charger is used.
Figure 2:
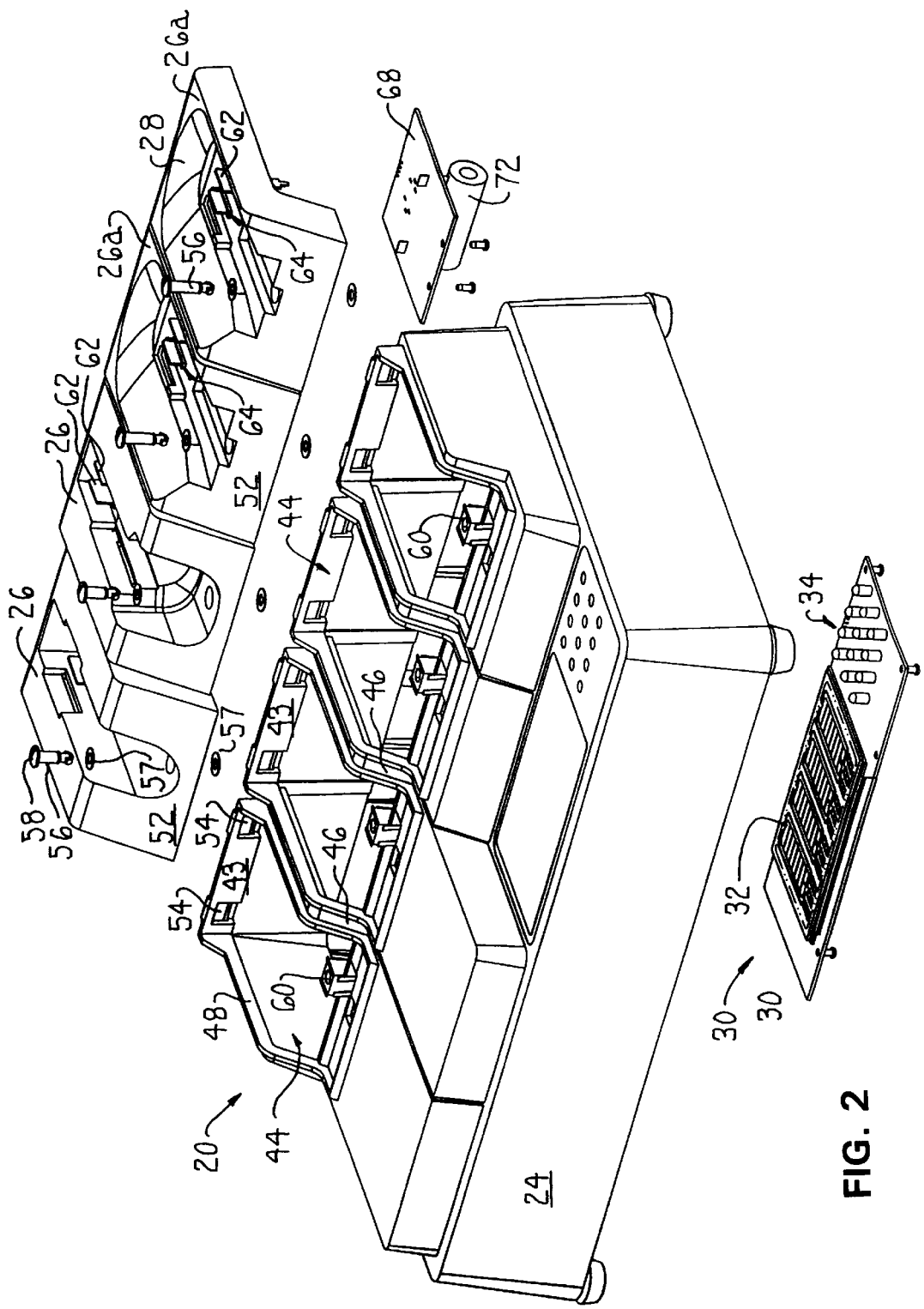
FIG. 2 is an exploded perspective view of the battery charger.

FIGS. 1 and 2 depict a battery charger 20 of this invention and a complementary rechargeable battery 22 especially designed for use with this charger. The battery charger 20 includes a base unit 24 in which the components internal to the charger are housed. Four modules 26, 26a are removably secured to the top of the base unit 24. Each module 26, 26a is formed with a socket 28, 28a, respectively, for receiving the head end of a complementary battery. A display unit 30 attached to the base unit 24 provides information about the batteries being charged. In the illustrated embodiment of the invention, display unit 30 includes an LCD display 32 that provides information about both the state of the battery and the number of times the battery has been charged. An LED array 34 provides an indication if a particular battery that is attached to a charger is being charged, is ready for use or needs to be replaced.

The illustrated battery 22 is representative of only one type of battery that can be used with battery charger 20. Battery 22 includes a body 36 in which its rechargeable cells as well as its other internal components are housed as will be described and illustrated hereinafter. The battery 22 also includes a head 38 which, when the battery is its normal orientation, is the top component of the battery. Seated inside separate slots formed in the head 38 are the external power terminals 40 (FIG. 8) of the battery. Power terminals 40 are the terminals through which the energy is stored in the battery by the charger 20. Current is drawn from the battery 22 through the power terminals 40 by the complementary power-consuming unit the battery is employed to energize. Battery 22 also has an exposed data terminal 266 (FIG. 8) the purpose of which will be explained hereinafter.

Each module 26, 26a is seated in a separate opening, referred to as pocket 44, formed in the top of the base unit 24. In the illustrated embodiment of the invention, the pockets 44 are located in the rear of the base unit 24. The individual pockets 44 are separated from each other by laterally extending webs 46. The base unit 24 is further formed so that a lip 48 extends around the front and sides of each pocket 44. Back walls 43 extend upwardly around the rear of the pockets 44.

Each module 26, 26a has a non-conductive shell 52 with front and side walls, (not identified) that seat over the lip 48 of the complementary pocket 44 in which the module is seated. The rear of each shell is formed with two tabs, (not illustrated) that seat in complementary slots 54 formed in adjacent back wall 43. A quarter-turn-screw 56 is mounted in the front end of the shell 52. The screw 56 has a head 58 that locks into a complementary socket 60 secured to the top surface of the base unit 24. Washers 57 are fitted around screws 56. Collectively, the tabs in the back of the shell and quarter-turn-screw 56 lock the module 24 in the complementary pocket 44 in which the module is seated.

The top surface of each shell 52 is shaped to define the module socket 28, 28a. More specifically, each socket 28 and 28a is shaped to receive the head of a particular battery. For example, module 26a has a shell 52 that defines a socket 28a designed to receive the head 38 of battery 22. Extending through the shell 52 into the socket 52 are power contacts 62. When a battery is seated in a module, the power contacts 62 engage the complementary terminals 40 of the battery. Opposed stabilization bars 63 are mounted in the shell so as to extend into the space of socket 28. Typically, each battery is formed with some opposed lips 262 (FIG. 8) that defines slots. When the battery is placed in the socket 28, 28a, the stabilization bars seat 63 in the slots as to prevent battery movement.

Some modules 26, 26a are also provided with one or more data contacts 64. The data contacts 64 abut complementary data terminals that are integral with the batteries 22. Module 26a, for example, is constructed so to have a single data contact 64 that is mounted to the portion of its shell 52 that defines the socket 28a. This data contact abuts data terminal 266 of battery 22.

Mounted inside each shell 52 is a module board 68. Each module board 68 carries the electrical components and conductors that are integral with each module 26, 26a. As will be discussed later by reference to FIG. 6, two of the main components carried on module board 68 are module memory 70 and a load resistor 72. As will be discussed in detail hereinafter, module memory 70 stores data that defines which process steps are executed to charge a battery and the charging currents that are applied during the charging process. The load resistor 72 is specific to each module 26 so that the power delivering capacities of different batteries with which the charger 20 is used can be accurately measured. Not illustrated is a male terminal connector that extends downwardly from the module board 68. The male terminal connector provides the conductive connections between the module 26 and the base unit 24.

Figure 3:
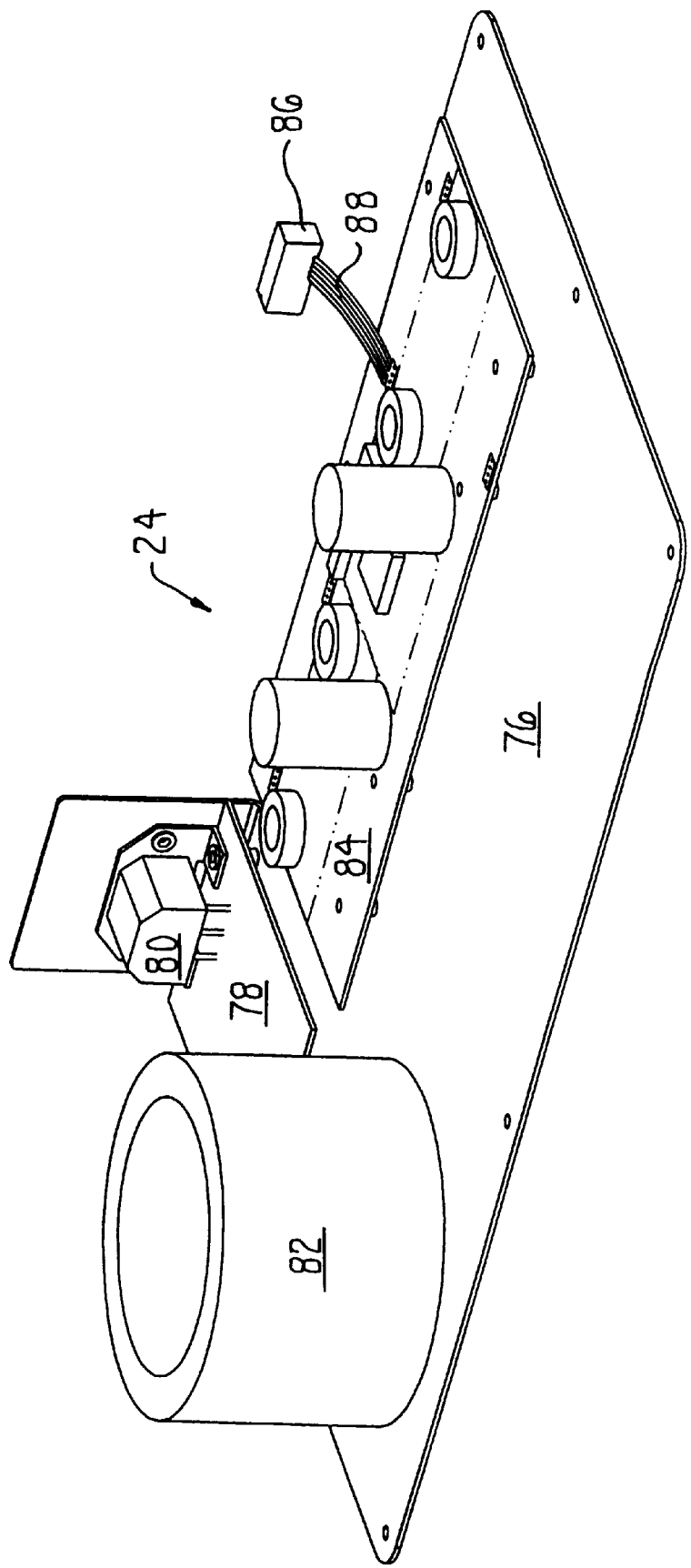
FIG. 3 is a perspective view of the main component boards internal to the battery charger.

The components internal to the base unit 24 will now be described by initial reference to FIG. 3. A tray 76 serves as the bottom support panel for the battery charger 20. One board mounted to the tray 76 is a line power board 78. The line power board carries a socket 80 to which an external line voltage is applied. A torrid-shaped transformer 82 is also mounted to the power board. The line voltage is applied to the transformer 82. Transformer 82, in turn, steps down the line voltage to levels suitable for rectification into DC voltages that are applied to the other components of the charger 20. A main board 84 is also mounted to tray 76. The main board 84 contains the current sources that are used to apply charges to the batteries. Main board 84 also supports the control circuit that both regulates the operation of the current sources and the presentation of information on the display unit 30.

Four female electrical sockets 86 are connected to tray 76 by separate flat cables 88 (one socket-cable pair shown). Each female socket 86 is connected to the designed to receive the complementary male terminal connector from one of the modules 26.

Figure 4:
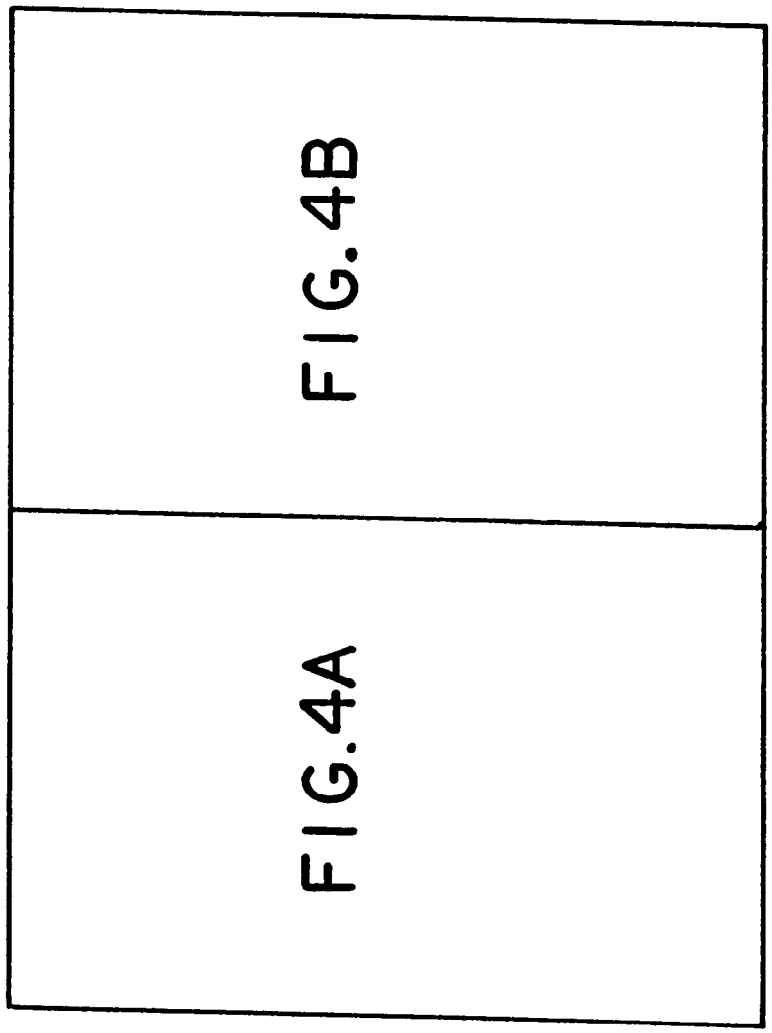
FIG. 4 is a blue print depicting how
Figure 4A:
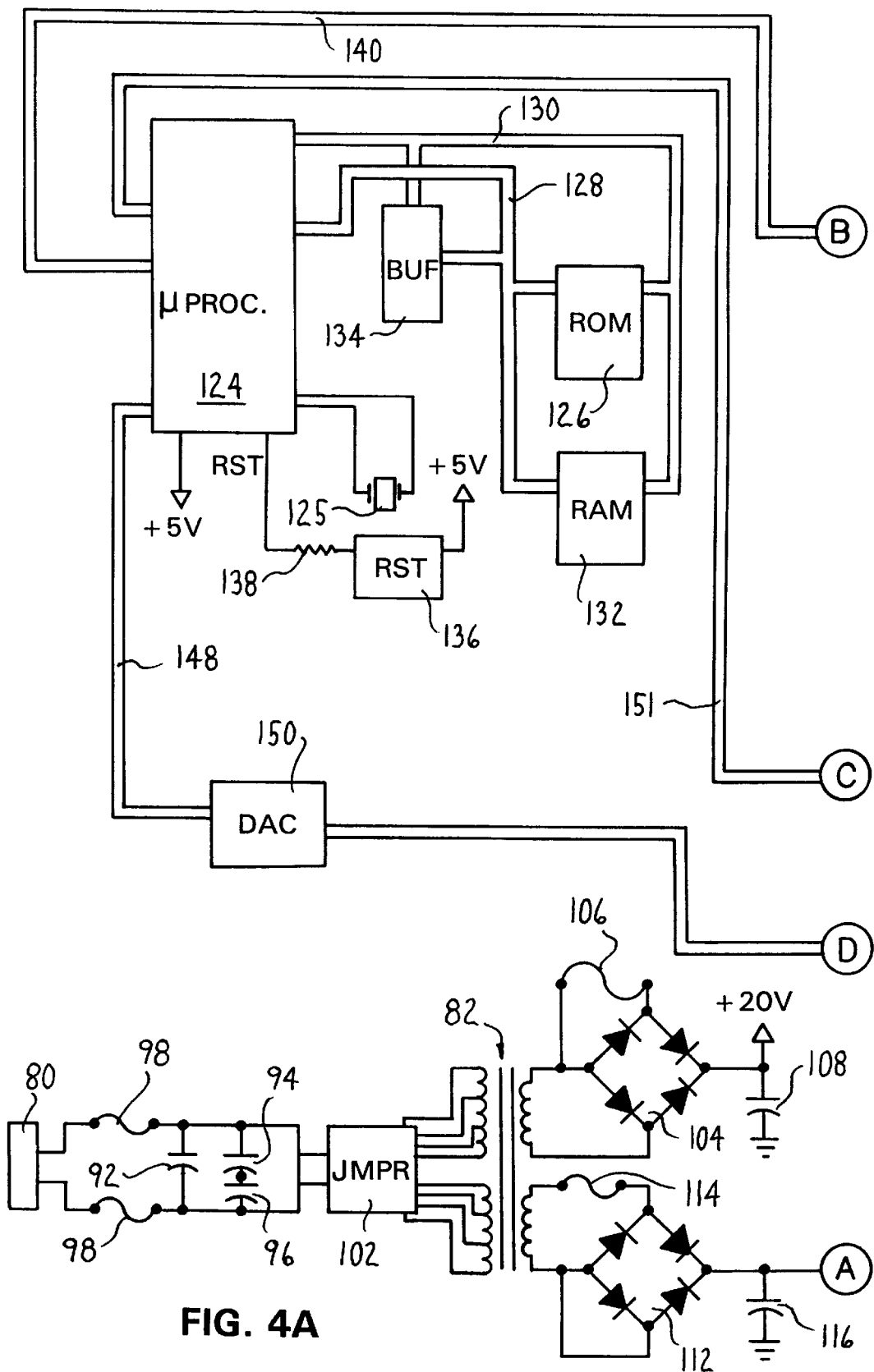
FIGS. 4A and 4B are assembled together to form a schematic and block diagram illustration of the circuitry internal to the battery charger.
Figure 4B:
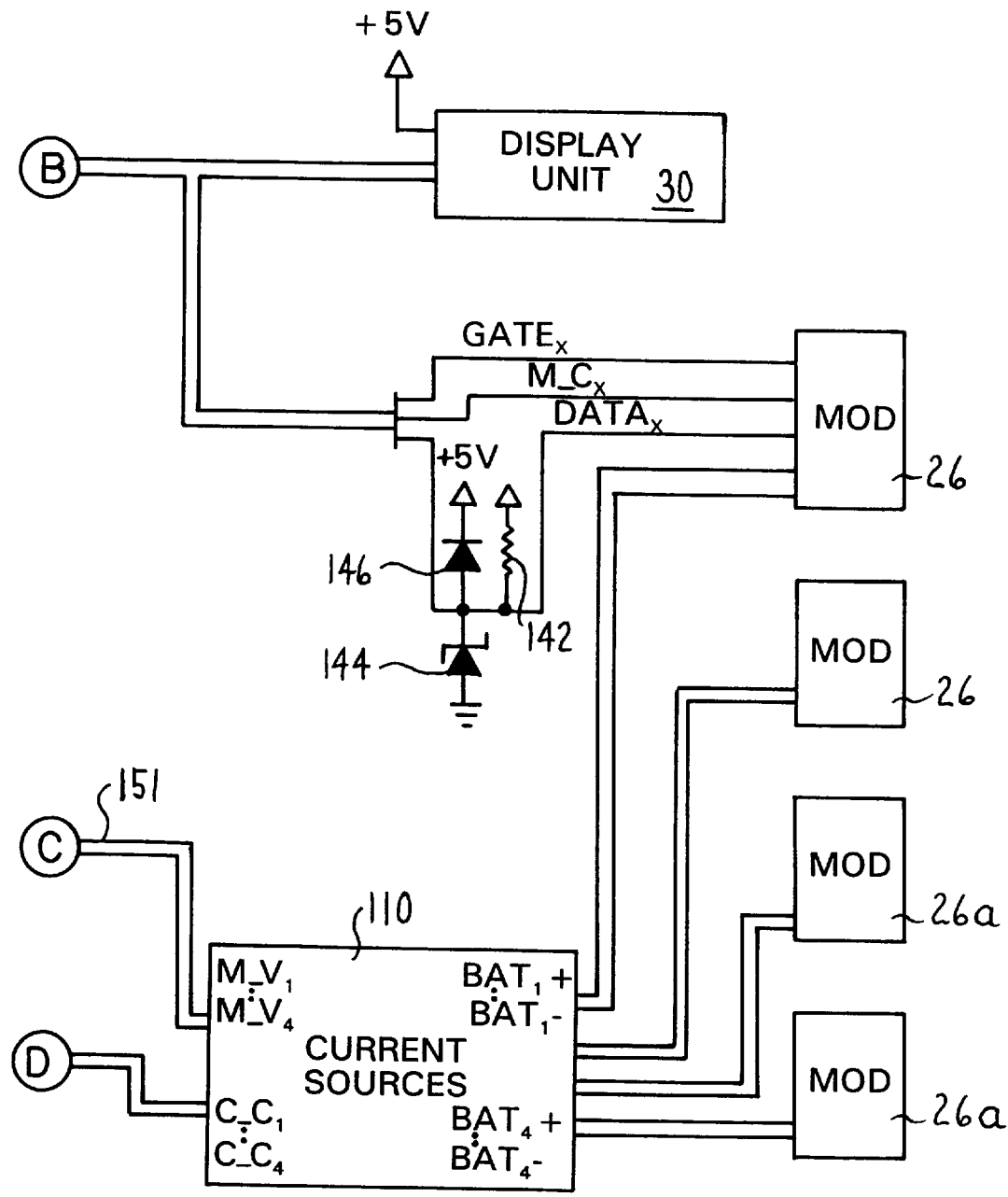
Figure 4B:
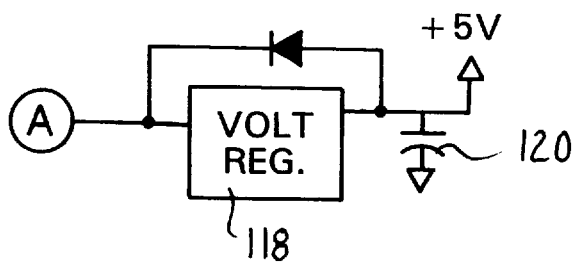

The FIGS. 4A and 4B, when assembled together, form a schematic and block diagram of the basic electrical components internal to base unit 24 which are now discussed. Line voltage is introduced into the circuit through socket 80. A capacitor 92 is tied across the terminals of socket 80. Two capacitors 94 and 96 are series connected together and are connected in parallel across capacitor 92. Collectively, capacitors 92, 94 and 96 filter noise present in the charger 20 so that is does not travel over the line over which the supply voltage is provided. Two fuses 98 are connected between socket 86 and capacitors 92, 94, 96 to prevent excess current from being applied to the charger 20.

After filtering, the line voltage is applied to transformer 82 through a jumper unit 102. Transformer 82 has two primary windings and two complementary secondary windings. The primary windings each have a number of different taps through which the line voltage is applied thereto from the jumper unit 102. The jumper unit 102 functions as a switch unit that is used to establish the portions of the primary windings to which the line voltage is applied to ensure that the proper voltages appear across the secondary windings. The setting of the jumper unit 102 is established as a function of the voltage level of the line voltage. The jumper unit 102 setting is typically established once, when the charger 20 is first installed at a facility.

The voltage across a first one of the secondary windings of transformer 82 is applied to a first bridge rectifier 104 through a fuse 106. The rectified output signal produced by bridge rectifier 104 is at 20 VDC. A capacitor 108 is tied between the output terminal of the bridge rectifier 104 and ground. Capacitor 108 filters 120 Hz ripple out of the 20 VDC rail signal. This output signal is the signal applied to current sources 110 that supply charging current to the batteries. (To simplify the depiction of the circuit, the 20 VDC power rail to which the 20 VDC is signal is applied to the current sources 110 is omitted.)

The voltage across a second one of the secondary windings of transformer 82 is applied to a second bridge rectifier 112 through a fuse 114. The output signal from the second bridge rectifier 112 is filtered through a capacitor 116 tied between the rectifier and ground. The filtered output signal serves the input signal into a voltage regulator 118. Voltage regulator 118 produces a relatively constant 5 VDC output signal. The output signal from the voltage regulator 118 is filtered through a capacitor 120 tied between the output terminal of the voltage regulator and ground. The output signal from voltage regulator 118 is applied to many of the other components of the charger as power and/or reference signal. (To simplify the depiction of the circuit, the 5 VDC power rail as well as most of the terminals to which the 5 VDC signal are applied are omitted.)

It should also be recognized that, in many preferred embodiments of this invention, the construction of the foregoing power supply circuit may vary from what has been described. For example, it may be desirable to provide transformer 82 with more than the two described primary/secondary windings subassemblies. Alternatively, it may be desirable to provide a switching power supply that can run on signals from 85 to 265 VAC without a switch. Integral with each of these assemblies would be an appropriate rectifier for establishing one or more of the internal power signals required by the charger 20. In these embodiments of the invention, jumper unit 102 may be used to establish to which winding subassemblies the line voltage is applied. Also, it may be desirable to provide a second voltage regulator, (not illustrated,) to the second bridge rectifier 112 to provide still another regulated power signal for use by the components internal to the charger. In some embodiments of the invention, the second voltage regulator produces an 8 VDC signal that is applied to some of the amplifiers internal to the current sources 110 as a $V^+$ supply voltage.

The current each current source 110 applies to the battery it is employed to charge is based on a control signal generated by a microprocessor 124. Microprocessor 124, in addition to including processing components, also includes internal analog-to-digital signal converters, (not illustrated). These A-to-D converters digitize signals from the modules 26 and current sources 110. The microprocessor 124 uses these received-and-digitized signals as feedback signals to regulate the charging of the batteries. One suitable microprocessor 124 that can be employed in the charging unit 20 of this invention is the 80C552 manufactured by Philips Semiconductor.

A clock signal is provided to microprocessor 124 by crystal 125. In preferred embodiments the invention, microprocessor 124 operates at a rate of 11.06 MHz.

A ROM 126, such as an EEPROM, is tied to the microprocessor 124 over both a combined address-and-data bus 128 and an address-only bus 130. The ROM 126 stores the permanent operating instructions for the microprocessor 124. A RAM 132 is also connected to the microprocessor over buses 128 and 130. The RAM 132 serves as the temporary store for the data microprocessor 124 generates internally during operation of the battery charger 20 and the data read from the module memory 70. A buffer 134 is also provided. Buffer 134 functions as an address latch that locks the upper parts of the memory addresses. Buffer 134 is connected to microprocessor 124 and memories 126 and 132 through buses 128 and 130.

A reset chip 136 is also connected to microprocessor 124. The reset chip 136 asserts a RESET (RST) signal to microprocessor 124 through a resistor 138 whenever the voltage on the 5 Volt rail drops below a select value. In one embodiment of the invention, the RESET signal is asserted whenever the 5 Volt rail voltage drops below 4.75 VDC.

Microprocessor 124 receives data from and sends control signals to the modules 26 through a main bus 140. Specifically, microprocessor 124 receives data from each module 26 over a DATAx line connected directly to the module. (For simplicity, only the connection to a single module 26 is shown.) It will be observed that each DATAx line is tied to the 5 VDC voltage bus through a pull-up resistor 142. Voltage protection for each DATAx line is provided by a zener diode 144 which is tied between the line and ground. A diode 146 is tied between each DATAx line and the 5 VDC voltage bus to provide electrostatic protection.

Each module 26 is also capable of sending the microprocessor 124 an analog data signal over a MODULE_CONTROLx (M_Cx) line also part of the main bus 140. (For simplicity, only a single MODULE_CONTROLx line is shown). The type of data carried over the MODULE_CONTROLx line is a function of the specific module 26 coupled to the line. For example, some modules 26 are provided with temperature sensors to monitor the temperature of the load resistor 72 integral with the module. When one of these modules 26, 26a is coupled to base unit 24, the associated MODULE_CONTROLx line serves as a conductive path over which the analog output signal from the temperature sensor is applied to the microprocessor 124.

Other modules 26 are provided with voltage dividers or secondary load resistors across which the voltage across the battery is measured. The MODULE_CONTROLx lines to which these modules 26, 26a are connected serve as the conductive paths over which signals representative of the measured voltages are forwarded to the microprocessor. The analog-to digital signal converters internal to the microprocessor 124 convert the received analog signals into a digital form that are used by the logic components of the microprocessor.

The display unit 30 also receives signals from the microprocessor 124 over the main bus 140. More specifically, microprocessor 124 generates the control signals to the display unit 30 to cause the display unit to present information to the end-user about the charge state of the batteries being charged by the battery charger 20. In one embodiment of the invention, the microprocessor generates serial clock and data signals to the display unit. More specifically, the data are forwarded to the display unit using the Philips I2C data transmission protocol. Display drivers internal to the display unit 30, upon receipt of this data, cause the appropriate LEDs to be illuminated and the appropriate images to be presented on the LCD display 32.

The microprocessor 124 also exchanges signals with the current sources 110. Specifically, the microprocessor generates a CURRENT_CONTROLx (C_Cx) signals to each of the current sources 110. The CURRENT_CONTROLx signal is the signal that establishes the amperage of the charging current the current source 110 should deliver to the battery 22 to which it is connected. In the depicted embodiment of the invention, the CURRENT_CONTROLx signals generated by the microprocessor 124 are serial, digital signals. The CURRENT_CONTROLx signals are generated over a single line that is part of a current control bus 148. The other signals microprocessor 124 generates over current control bus 148 are clock and data load signals. The second end of the current control bus 148 is tied to a digital-to-analog converter 150. Digital-to-analog converter 150, produces steady, latched versions of each output analog CURRENT_CONTROLx signal until a new digital version of each signal is received. The analog versions of the CURRENT_CONTROLx signals are the signals that are applied to the current sources 110 as control signals.

The microprocessor 124 receives from each current source a MEASURED_VOLTAGEx (M_Vx) signal. As will be discussed hereinafter, the MEASURED_VOLTAGEx signal can be a measure of the voltage across a battery as it is being charged. Alternatively, the MEASURED_VOLTAGEx signal is measure or the voltage across the load resistor 72 that is selectively tied across each battery to discharge the battery. Analog-to-digital signal converters internal to the microprocessor 124 convert the MEASURED_VOLTAGEx signals into digital form. In FIGS. 4A and 4B, the MEASURED_VOLTAGEx are forward to microprocessor 124 over a parallel analog signal bus 151.

Figure 5:
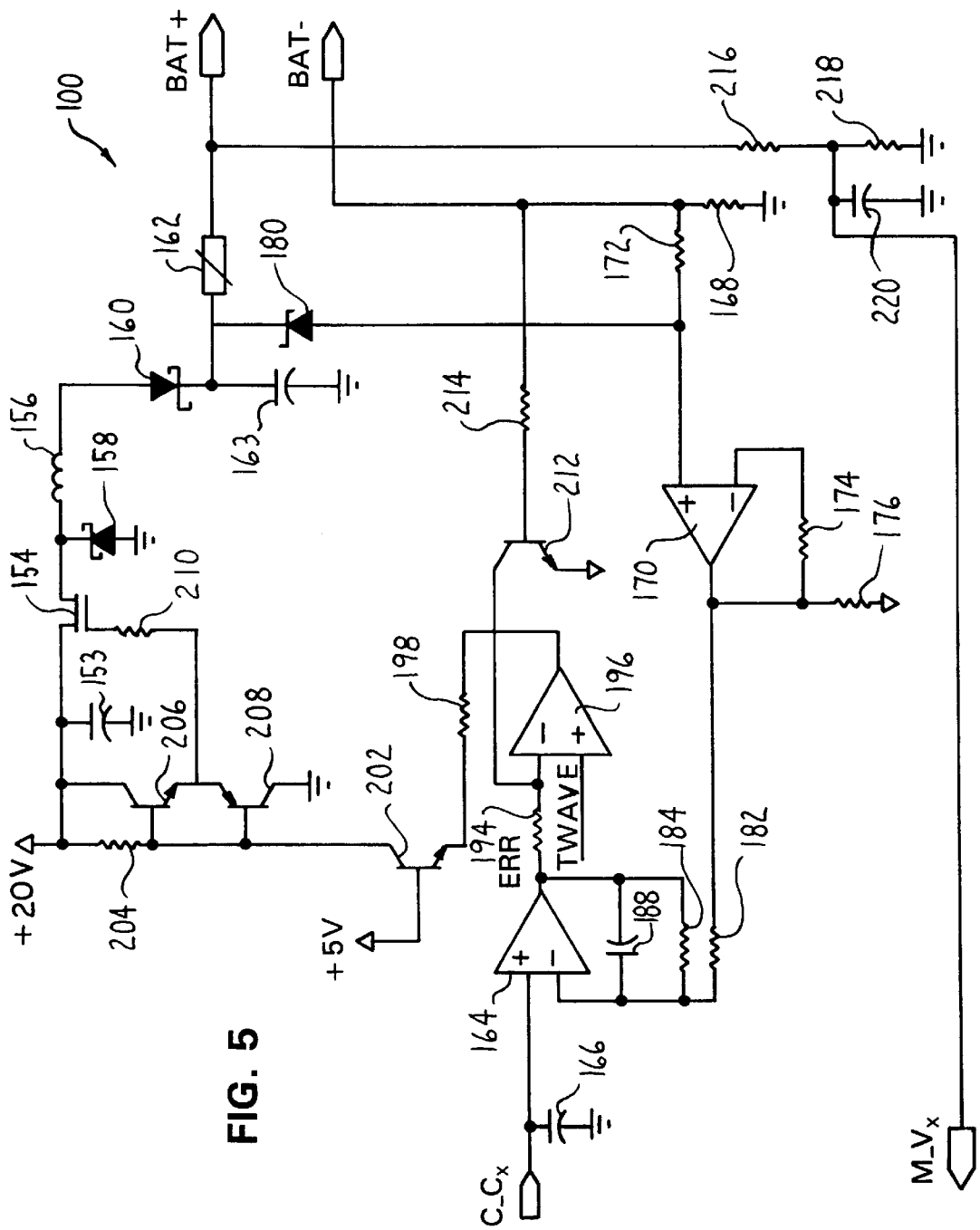
FIG. 5 is a schematic diagram of a single one of the current sources internal to the battery charger.

The components internal to a single one of the current sources 110 are now described by reference to FIG. 5. Initially, it should be understood that each current source 110 is capable of generating a variable charging current. In some embodiments of the invention this current is between 0 and 10 Amps; in more preferred embodiments, the current is between 0 and 2 Amps. The 20 VDC signal is smoothed by a capacitor 153 tied between the 20 VDC rail and ground and is applied to the battery through a buck converter. The buck converter consists of a FET 154, an inductor 156 and a Schottky diode 158. Diode 158 is a reverse biased catch diode that is tied between the junction of FET 154 and inductor 156.

The current from inductor 156 is applied to a BAT+ terminal of the current source 110 through a forward biased diode Schottky 160 and a fuse 162. The insertion of forward biased diode 160 into the current source 110 prevents the charge stored in the battery from flowing back through the current source and powering the charger 20. Fuse 162 is a current-triggered fuse that prevents excess current flow into the battery 12. A capacitor 163 is tied between the cathode of diode 160 and ground. Capacitor 163 performs a final smoothing of the charging current that is applied to the battery.

The signal that turns on FET 154 is an ERROR (ERR) signal. The ERROR signal is generated by comparing the current flow into the battery with the intended current flow as indicated by the CURRENT_CONTROLx signal applied to the current source 110. This comparison is performed by an amplifier 164. The CURRENT_CONTROLx signal is applied to the non-inverting input of amplifier 164. Initially, prior to the CURRENT_CONTROLx signal being applied to the amplifier 164, spikes are removed from the signal by a capacitor 166 tied between the input of the amplifier and ground.

The current flow into the battery 22 is measured by monitoring the voltage across resistor 168. Resistor 168 is connected between a BAT− terminal of the current source 110 and ground. The voltage present at the junction of the BAT− terminal and resistor 168 is applied to the non-inverting input of amplifier 170 through a resistor 172. A resistor 174 is connected between the output and inverting input of amplifier 170. A resistor 176 is connected between the output of amplifier 170 and ground. Collectively, resistors 174 and 176 establish the gain of the amplifier 170.

The cathode of a reverse biased zener diode 180 is tied to the junction of diode 160 and fuse 162. The anode of diode 180 is tied to the noninverting input of amplifier 170. In the event the voltage of the signal applied to the battery exceeds 20 volts, the current flows through diode 180. Thus, when there is no battery in socket 28, diode 180 serves as a voltage regulator to prevent the voltage from rising on the power contacts 62.

The signal produced by amplifier 170 is applied to the inverting input of amplifier 164 through a resistor 182. A resistor 184 and a capacitor 188 are connected in parallel between the output terminal of amplifier 164. Resistor 182 and capacitor 188 form an integrator with amplifier 164. Resistor 184 provides a DC feedback signal to amplifier 164. Collectively, resistors 182 and 184 and capacitor 188 ensure that the ERROR signal produced by amplifier 164 stays within a select range.

The ERROR signal produced by amplifier 164 is applied through a resistor 194 to the inverting input of a comparator 196. A fixed-frequency triangle wave of between 55 to 65 Khz is applied to the inverting input of comparator 196. A triangle wave generator, (not illustrated) generates this latter signal. Comparator 196 produces output pulses that have an "on" duty cycle that is a function of the magnitude of the ERROR signal. Specifically, as the level of the ERROR signal increases, the fraction of time the on pulses are produced decreases.

The output pulses produced by comparator 196 are applied through a resistor 198 to the emitter of an NPN transistor 202. The collector of transistor 202 receives the 20 VDC rail voltage through a resistor 204. The base of transistor 202 receives the 5 VDC signal. When the output of comparator 196 is low, transistor 202 is turned on. Collectively, resistors 198 and 204 level shift the 20 VDC voltage to a set voltage below this level. In some embodiments of this invention, this difference is 10 VDC. When the output of comparator 196 is low, transistor 202 is turned on. The turning on of transistor 202 causes this shifted voltage to appear at its collector.

The voltage present at the collector of transistor 202 is applied to the bases of two series-connected transistors 206 and 208. The collector of transistor 206 is tied to receive the 20 VDC rail signal. The emitter of transistor 206 is tied to the emitter of transistor 208. The collector of transistor 208 is tied to ground. The current-boosted signal present at the emitter-emitter junction of transistors 206 and 208 is applied to the gate of FET 154 through a resistor 210.

A transistor 212 prevents the current source 110 from applying excess current to a battery when it is initially seated in the module 26. The voltage present at the BAT− terminal is applied to the base of transistor 212 through a resistor 214. The collector of transistor 212 is tied the junction of resistor 194 and comparator 196; the emitter of the transistor is tied to ground.

Prior to the seating of the battery in the socket 28, there is no current flow between the BAT+ and BAT− terminals. Consequently, in order to drive the voltage difference between its inputs to zero, amplifier 164 may produce a relatively high ERROR signal. This means that when a battery is initially placed in the socket 28, the current source may attempt to apply a relative high current to it. However, when a battery is initially seated in the socket, the voltage across resistor 168 rapidly rises above the 0.6 VDC level required to turn on transistor 212. The turning on of transistor 212 forces the ERROR signal to ground before it is applied to the comparator 196. The forcing of the ERROR signal to ground causes comparator 196 to produce a constant-state high signal that turns transistor 202 off. The turning off of transistor 202 turns of FET 154 to prevent the battery from initially receiving a large current flow.

The rapid turning off of current flow through the battery 22 causes the voltage across resistor 168 to fall below the turn-on voltage level of transistor 212. Once these events occur, the ERROR signal is within its normal range and the current source 110 then applies a charge at an appropriate level to the battery. It should be recognized that the voltage across resistor 168 may not rapidly drop to below the level at which transition 212 is turned off. Thus, transistor 212 may slowly transition from the full-on state to the full-off state. Owing to this slow transition, there may be a slight delay in the time it takes for the full measure of the ERROR signal to be again applied to comparator 196.

Current source 110 also includes two series-connected resistors 216 and 218 that are tied between the BAT+ terminal and ground. The MEASURED_VOLTAGEx signal is the voltage preset at the junction between resistors 216 and 218. The MEASURED_VOLTAGEx signal is filtered by a capacitor 220 that is connected across resistor 220.

Figure 6:
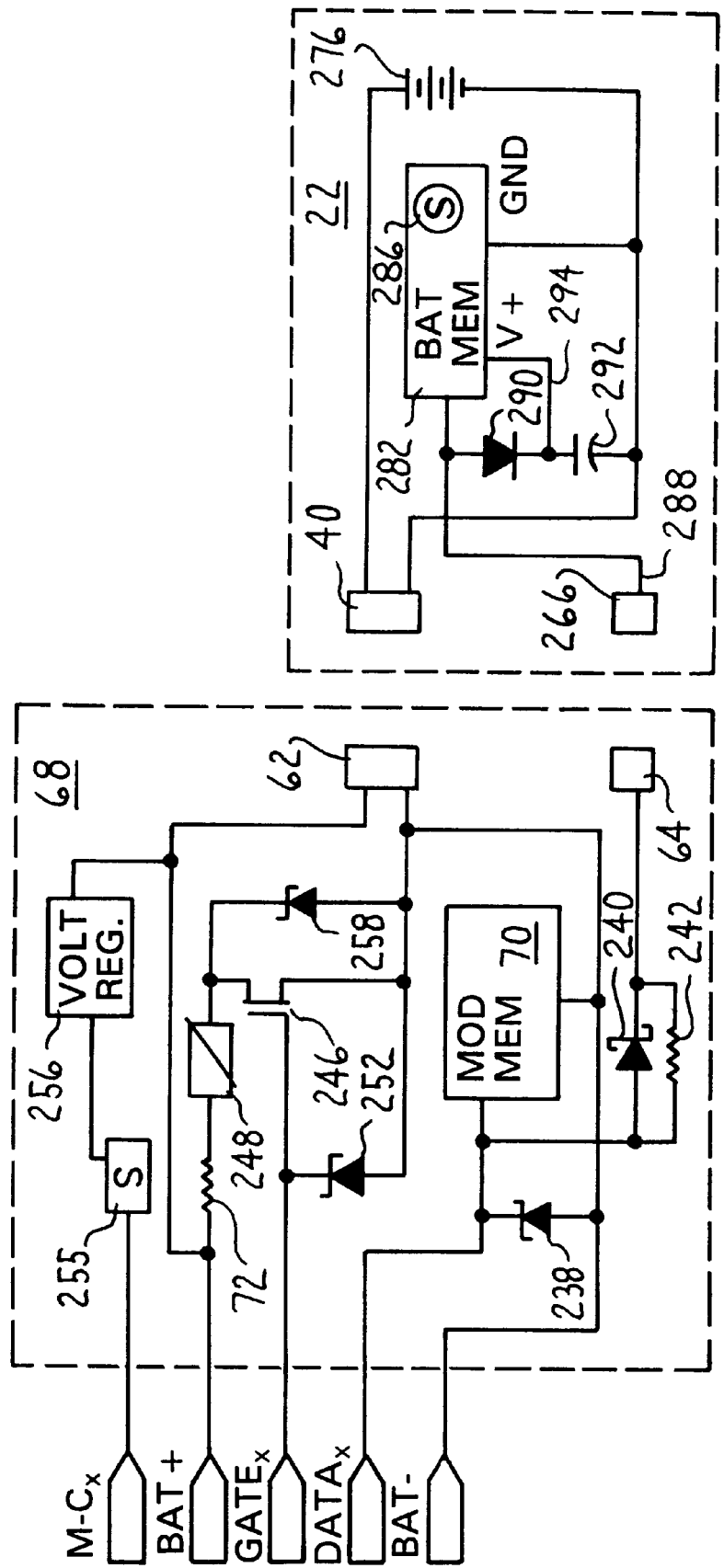
FIG. 6 is a schematic diagram of the circuitry integral with a removable module that is attached to the charger and of the circuitry internal to the battery.

The circuit carried by the module board 68 internal to each module 26 is now described with reference to FIG. 6. The charging current is applied to the battery through a BAT+ terminal and to a positive power contact 62. (In FIG. 6, the positive and negative power contacts 62 are represented as a single block element). A ground is also established between the current source 110 and the battery 12 through the module board 68. This path extends from a BAT− terminal integral with the module board 68 to a negative power contact 62.

The module board 68 also carries the module memory chip 70 and the load resistor 72. The module memory 70 is a ROM in which data are read out serially. A DATA terminal provides a conductive port through which the microprocessor 124 accesses the data stored in the module memory 70. It will be further noted that the ground pin of the module memory is connected to the BAT− terminal of the module board 68. The data in the module memory 70 are read prior to the application of a charging current to the battery. When the battery is not being charged, the BAT− conductor internal to the base unit 24 functions as a virtual ground. At these times, the BAT− conductive path established on the module board 68 functions as a ground reference upon which the module memory 70 processes signals.

One suitable ROM that can be employed as the module memory 70 is the DS2505 manufactured by Dallas Semiconductor. This particular ROM has an internal capacitor that stores the energy received from the base unit 24 over the DATAx line during read cycles. The ROM capacitor, in turn, draws on this stored charge to energize the other components of the ROM.

In the depicted circuit, it will be noted that a branch of the module board DATA conductor extends to a data contact 64. This branch is provided in modules 26a that are intended for use with batteries that, as discussed hereinafter, contain internal memories. In these particular modules 26a, a reverse-biased zener diode 238 extends from the DATA conductor to the BAT− conductor. Also, integral with the branch of the DATA conductor that extends to battery data contact 64 is a forward-biased Schottky diode 240 and a resistor 242 that is connected across diode 240. In the event the exposed portion of the module data contact 64 is ever shorted to the exposed BAT+ power conductor 62, diodes 238 and 240 and resistor 242 prevent excessive voltages from traveling downline along the DATAx conductor.

The load resistor 72 is connected at one end to the BAT+ terminal. The opposed end of the load resistor 72 is connected to the drain of a normally open FET 246 through a current-set fuse 248. The source of FET 246 is connected to the module board conductor that leads to the BAT− terminal. The gate of FET 246 is tied to a GATE terminal integral with the module board through which the GATEx signal from the microprocessor 124 is received.

The current-set fuse 248 provides protection for the module board in the event FET 246 breaks down and stays in the closed state. The current-set fuse 248 opens upon when the surrounding ambient temperature exceeds a select level. If FET 246 breaks down causing current to continually flow through the load resistor 72, the temperature of the load resistor will rise. Should load resistor 72 temperature rise above a select level, current-set fuse 248 opens to prevent further current flow.

A Schottky diode 252 is reverse biased between the gate and source of FET 246. A second Schottky diode 258 is reverse biased between the source and drain of FET 250. Diodes 252 and 258 provide voltage protection for FET 252 in the event the module board 68 is exposed to a static electric discharge.

The illustrated module board 68 also includes a temperature sensor 255. Physically, temperature sensor 255 is mounted close enough to the load resistor 72 to provide an output signal representative of load resistor temperature. The output signal from the temperature sensor 255 is applied to the complementary MODULE_CONTROLx line of the base unit main bus 140 through a MODULE_CONTROL terminal. A fixed voltage energization signal is applied to the temperature sensor 255 from a voltage regulator 256 also mounted to module board 68. Voltage regulator 256 receives its power input directly from the BAT+ conductor.

Figure 7:
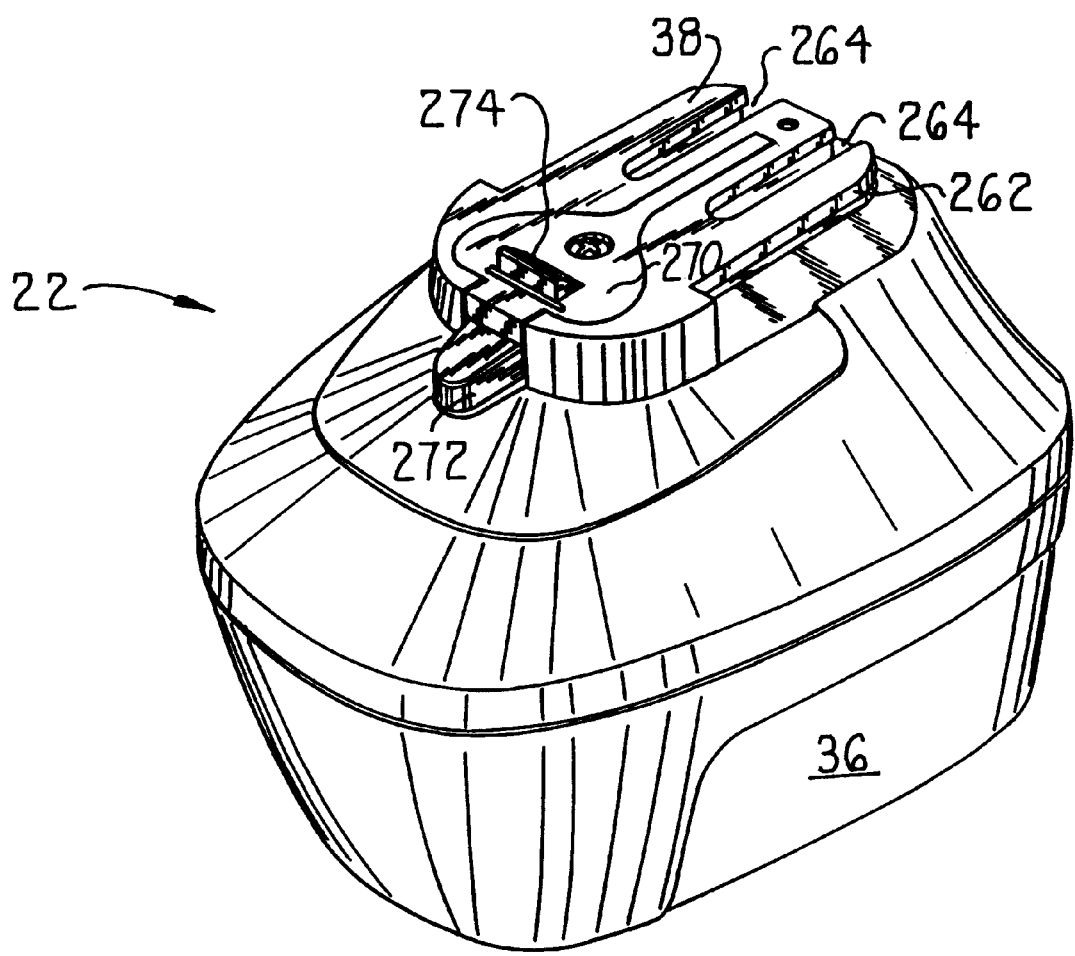
FIG. 7 is a front perspective view of the rechargeable battery especially designed for use with the battery charger of this invention.
Figure 8:
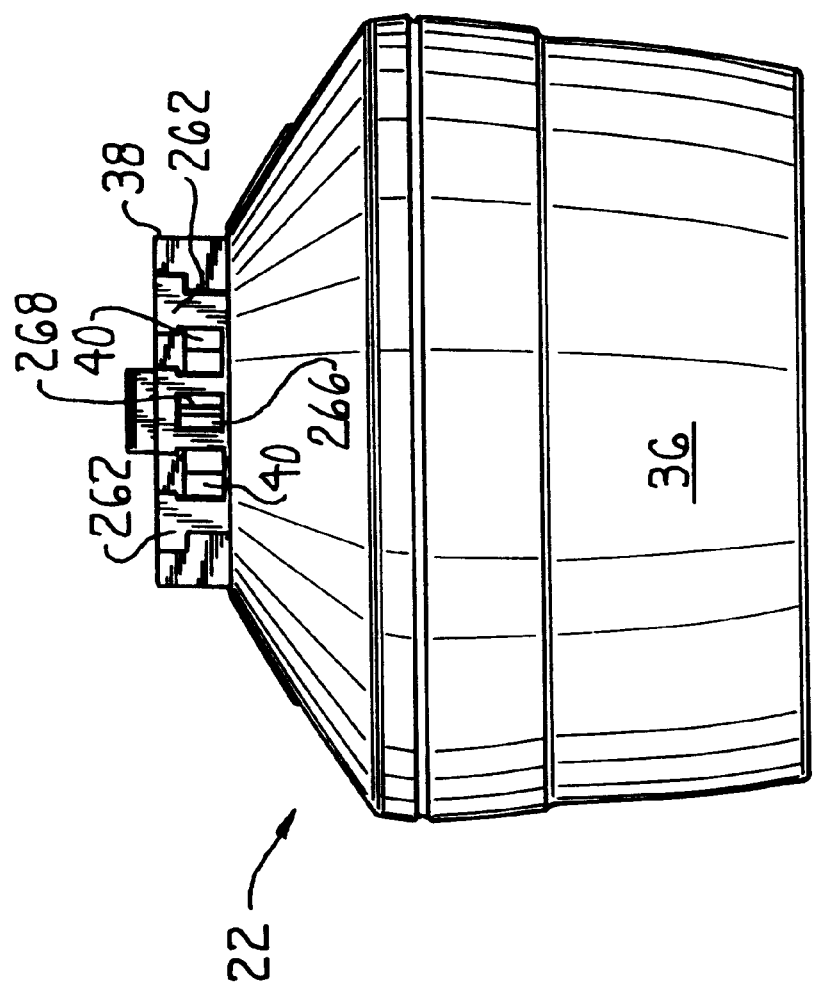
FIG. 8 is a rear view of the battery.

The battery 22 especially designed for use with battery charger 20 of this invention is now described in greater detail by initial reference to FIGS. 7 and 8. The upper surface of the head 38 of the battery 22 is provided with outwardly directed lips 262. The lips define slots, not identified, in which the stabilization bars 63 are located when the battery 22 is seated in the socket 28. The power terminals 40 are seated in slots 264 formed in the head 38.

Battery 22 is also provided with data terminal 266. The data terminal 266 is seated in an opening 268 formed in the rear of battery head 38. When battery 22 is seated in socket 28a, a conductive path is established between data contact 64 of the module 68 and data terminal 266 of the battery. As will be discussed hereinafter, the data contact 64-data terminal 266 conductive path is the path over which data stored in the battery are transferred to the battery charger 20.

The depicted battery 22 is provided with a tongue 270. The tongue 270 is seated in an opening forming in the head 38, and is normally flush with the top of the head (opening not identified). Tongue 270 is pivotally attached to the rear of the head 38. The tongue 270 is formed with a release tab 272 located forward of the head 38. A triangularly shaped engagement tab 274 is formed integrally with the tongue and extends upwardly from the top surface of the tongue adjacent the front of the head 38. Tongue 270 and the associated components facilitate the locking of the battery to the complementary tool the battery is used energize and the release of the battery from the tool.

Figure 9:
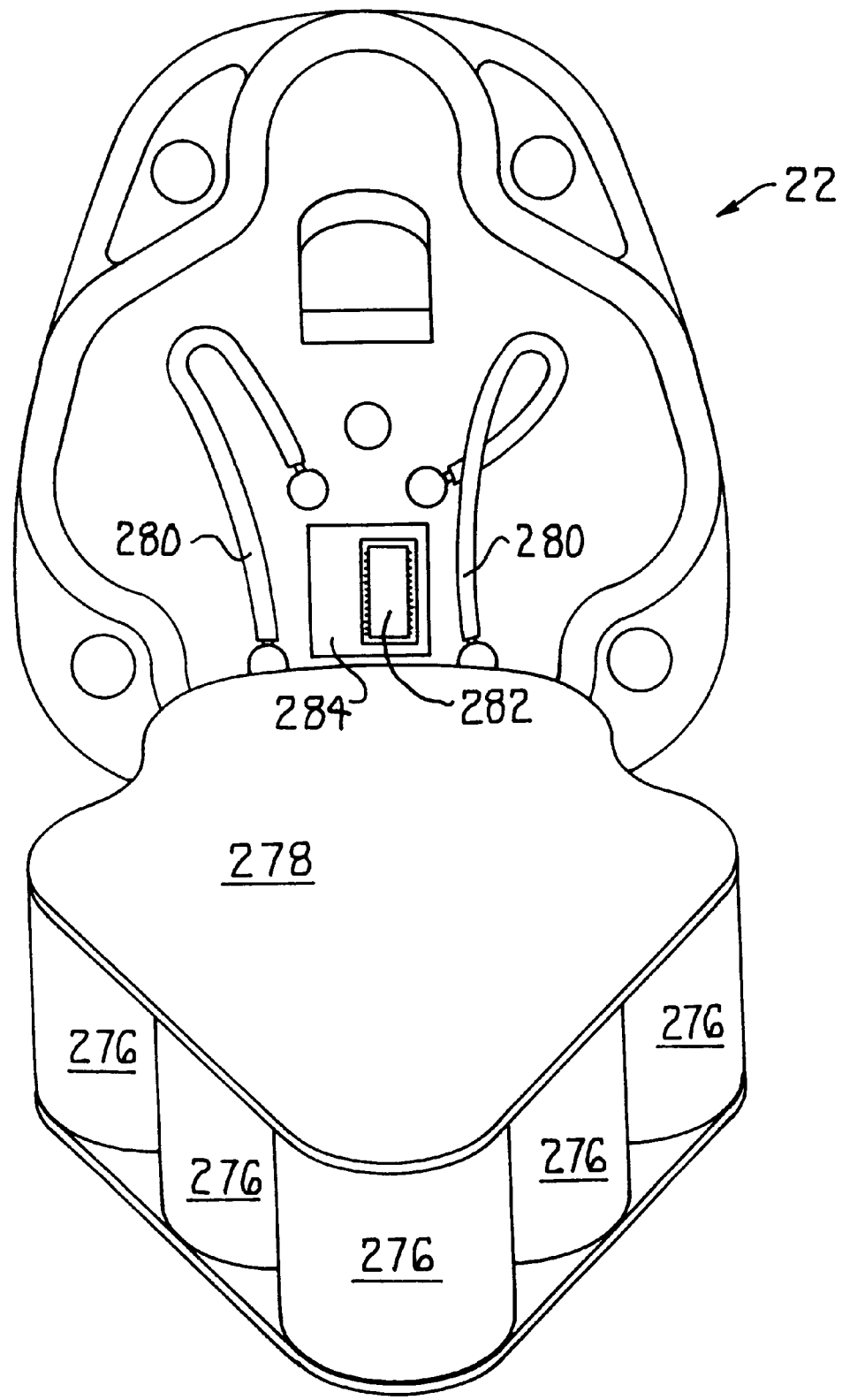
FIG. 9 is a view of the components internal to the battery.

As seen by FIG. 9, located inside the body 36 of the battery 22 are a number of rechargeable NiCd cells 276. Binders 278 located above the top and bottom of the cells 276 hold the cells together so that they form a single cell cluster. Conductors 280 connect the cells 276 to the power terminals 40.

Also disposed inside the battery 22 is a battery memory 282. Battery memory 282 is mounted on a small printed wiring board 284 located on top of cells 276. One suitable memory for battery memory 282 is memory DS2434S manufactured by Dallas Semiconductor. Memory 282, has both electrically erasable-programmable and random access memory locations for storing data. Internal to battery memory 282 is a temperature sensor 286 (FIG. 6.)

Returning to FIG. 6, the circuitry internal to the battery 22 is now discussed. The cells 276 are shown as being connected together in series, however that need not always be the case. The positive and negative terminals of the cells 276 are connected to the positive and negative power terminals 40, (the power terminals are shown as a single block). Data addresses are supplied to and data are read from the battery memory 282 over a serial data line 288 that extends between data terminal 266 and the battery. The ground terminal of battery memory 282 is tied to the conductor that extends between negative terminal of the cells 276 to the negative power terminal 40.

A forward biased diode 290 extends from data line 288. A capacitor 292 extends between the cathode of diode 290 and the ground line connected to the negative power terminal. A power line 294 extends between the diode 290-capacitor 292 junction and the V⁺ terminal of battery memory 282 to which the power supply signal for the memory is applied. When commands and address data are supplied to battery memory 282, the energy contained in the high portion of those signals is stored in capacitor 292. The stored energy is then used by the battery memory 282 to energize the memory during the cycles in which data is read from or written to the battery or an output signal representative of battery temperature is required.

With this understanding of the hardware internal to the charger 20 and battery 22 of this invention, the process by which a battery is charged is now described. Generally, a current source 110 charges a battery during an ordered set of charging states. During an individual charging state, the battery is discharged, the battery is charged and/or the battery's stored energy is measured. Microprocessor 124 cycles each current source 110 through the charging states. The microprocessor 124 more specifically controls the charging, so that when a current source is in a specific charging state, current is applied to or drawn from the associated battery according to a specific set of instructions. Each set of instructions comprises a number of process steps that are executed in a specific sequence to ensure that the battery is properly charged. Hereinafter, each set of instructions is referred to as a "instruction sequence". While individual instruction sequences may contain some identical process steps, the order in which those steps are executed varies between the instruction sequences.

The data describing the process steps executed by the charger when it cycles through the individual instruction sequences are stored in the ROM 126 internal to the charger 20. The ROM 126 also stores that instruction-containing data for the individual process steps that are executed during the cycling through of the instruction sequences.

Data indicating the particular instruction sequences through which a current source 110 is cycled as it charges a battery are stored in the memory 70 of the module 26 with which the battery is used. The module memory 70 also stores data that describe the particular parameters of the process steps that are to be executed during each instruction sequence. When the charger 20 is initially actuated, microprocessor 124 reads the data stored in each of the module memories 70. Then, when a battery is placed in the socket 28, 28a of a module 26, 26a microprocessor 124 issues the appropriate control signals to cycle the current source 110 and battery through the specific instruction sequences required to properly charge that battery.

If the battery has a memory, upon the seating of the battery in the module socket 28a, the data in the battery memory 282 are read. After these data are read, microprocessor 124 verifies from the data that the appropriate type of battery has been seated in the module and that the battery memory contains the appropriate information needed to properly charge the battery. Microprocessor 124 verifies the battery is an appropriate battery for charging by comparing a code stored in a dedicated data field in the battery memory 282 to a list of authorized codes stored in the module memory 70. Microprocessor 124 verifies the battery memory 282 contains the appropriate data by checking to ensure that the data corresponds to the data required by the microprocessor to regulate the charging of the battery.

It should further be understood that, when the charger 20 and current source 110 are in a particular state, the battery coupled to the current source is also in that charging state.

The charging states through which a current source 110 is cycled are now described by reference to the basic contents of the memory module 70, depicted by FIG. 10. Memory module 70 includes a set of state files 302–316. Each state file 302–316 contains data that identifies the specific instruction sequence that contains the instruction set through which the battery is cycled when it is in a particular state. Each state file 302–316 also contains data describing the characteristics of the process steps that are to be executed by the charger 20 is it cycles through the process steps that comprise the specified instruction sequence. The data also specifies the exit conditions under which the charger 20 should exit the state. Additional data indicate the next state the charger 20 should enter when a specific exit condition occurs.

Figure 10:
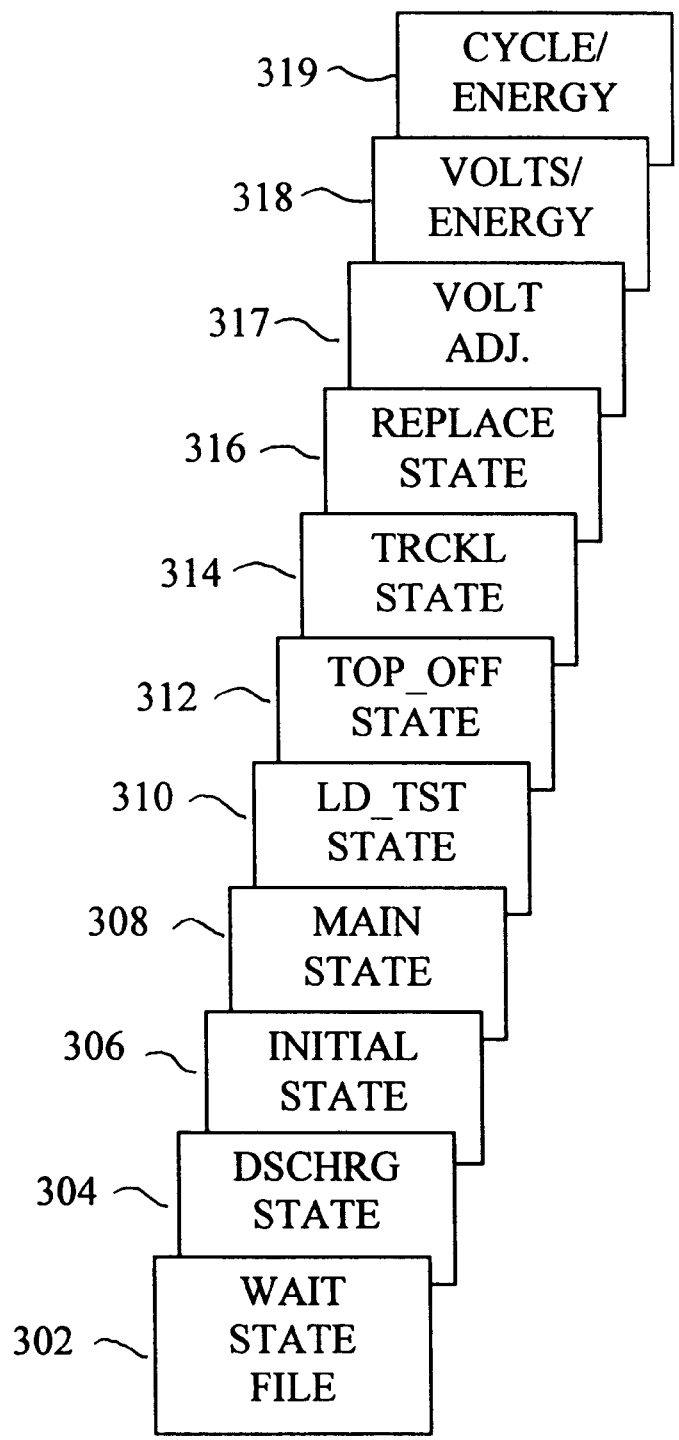
FIG. 10 is a diagram of the files disposed in the memory of the removable module of this charger.

The first one of the state files depicted in FIG. 10 is the wait state file 302. The wait state is also sometimes referred to as the open-socket state. A current source 110 is considered in the wait state when there is no battery seated in socket 28, 28a associated with the current source. The second state file is a discharge state file 304. This is an optional state through which only some batteries are cycled. The current source 110 enters the discharge state when, the battery with which it is being used is designed to be discharged before it is supplied with a charging current.

The third and fourth state files are, respectively, the initial state file 306 and the main state file 308. In the initial state, the current source 110 supplies the battery with a low level current until a select exit condition occurs. Normally, the current source 110 exits the initial state and enters the main state. In the main state, the current source 110 applies a larger current to the battery to fully charge it as quickly as possible.

A load test file 310 contains data related to the load testing of the fully charged battery. This load testing occurs after the battery is fully charged. Once the battery is load tested, the current source 110 enters a top-off state to replace the charger lost during load testing. The data which regulates this toping off is stored in a top off state file 312. Once the battery is topped-off, the current source 110 enters a trickle state. In the trickle state, a small current is applied to the battery to prevent it from losing its charger. A trickle state file 314 holds the data used to regulate the operation of the charger during this state.

As seen in FIG. 10, module memory 70 includes a replace state file 316. The current source enters the replace state when, it has been determined that the battery coupled to the current source 110 cannot hold a charge needed to usefully energize a power tool.

Three additional files 317, 318 and 319 internal to memory module 70 are also shown. The data stored in these files will be discussed hereinafter.

Figure 11:
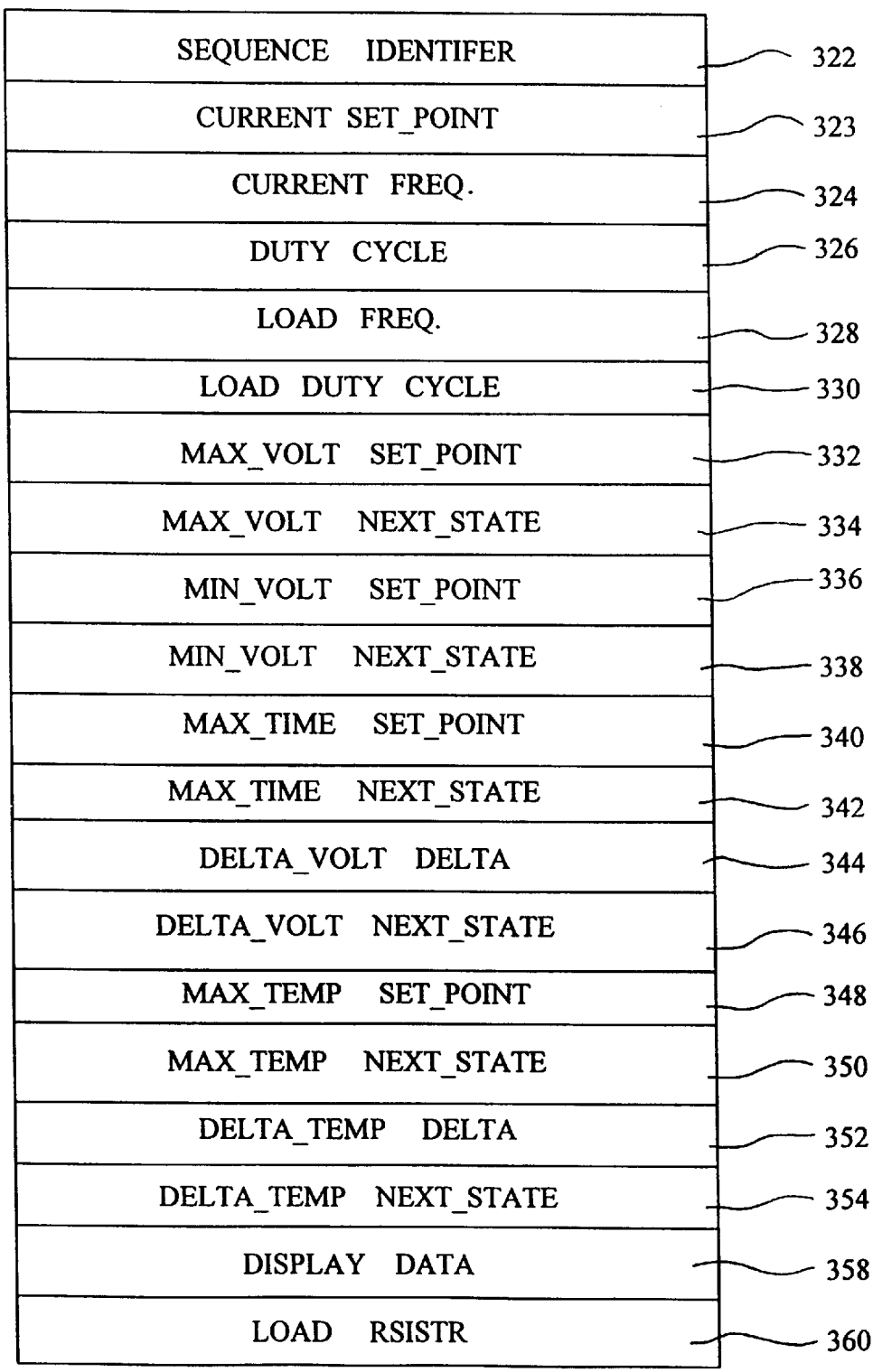
FIG. 11 is a diagram of the data fields that comprise a single state file internal to the module memory.

FIG. 11 depicts the fields within one of the largest state files, a main state file 308. The illustrated main state file 308 contains the data required by the microprocessor 124 to execute the process steps that comprise one instruction sequence that may be executed during the main state charging of a battery. As discussed hereinafter, when other instruction sequences are executed, microprocessor 124 may require different data to execute the process steps that comprise those sequences. The main state files 308 associated with these instruction sequences contain different data.

The first data field in the depicted main state file 308 is the sequence identifier field 322. Sequence identifier field 322 contains data that identifies the specific instruction sequence that contains the instructions executed by the microprocessor 124 when the battery is in that particular charging state. The second data field is the current set point field 323. The data in this field 323 indicates the current that should be supplied to the battery with which the module is associated. Microprocessor 124, based on the data contained in the current set point field 323, establishes the CURRENT_CONTROLx signal for the current source 110 with which the module memory 70 is associated.

The next two fields are a frequency of current field 324 and a current duty cycle field 326. Fields 324 and 326 contain data that, collectively, indicate how often the current should be applied to the battery and for long it should be applied to the battery each time it is applied. Microprocessor 124 uses the data in fields 324 and 326 to determine the rate and duty cycle of the CURRENT_CONTROLx signal to, in turn, cause the charging current to be appropriately cycled.

Main state field 308 also contains a load frequency field 328 and a load duty cycle field 330. Field 328 contains data that indicates how often, during the main state charging of the battery, the charging current should be turned off and the battery tied to the load resistor 72. Field 330 indicates for how long during the battery should be tied to the load resistor 72 prior to the resumption of the application of the charging current. Load frequency field and load duty cycle field 328 and 330, respectively, are provided because the charging process of some batteries require them to periodically discharge a small amount of current during the charging process.

The next fields, fields 332–354, are generally referred to as exit condition fields. These fields contain data that describes the set point conditions that need to occur before the current source 110 should exit the charging state it currently is in and enter the next charging state. Fields 332–354 further contain the data that indicates into which state the charger 20 should enter when the exit condition test results are positive.

The first exit condition fields are the maximum voltage set point field 332 and complementary maximum voltage next state field 334. The maximum voltage set point voltage field contains data indicating a particular maximum voltage for which the microprocessor 124 should test when it reads the battery voltage as the MEASURED_VOLTAGEx signal from the current source 110.

The maximum voltage next state field 334 contains data to indicate the next state the charger should enter if the measured voltage exceeds the above-specified maximum voltage. It should hereinafter be understood that the following next state fields 334, 338, 342, 346, 350 and 354 likewise contain similar information for the test point parameters with which they are associated. Accordingly, the contents of these fields will not be further described.

A minimum voltage set point field 336 contains data indicating a specific minimum voltage for which the microprocessor 124 should test when reading the MEASURED_VOLTAGEx signal. A maximum time set point field 340 generally indicates the maximum time the charger should remain in the main state. Microprocessor 124 tests for maximum time by monitoring an internal timer, or time data field, that is zeroed out and restated each time the current source 110 enters a new state.

A delta voltage field 344 contains data upon which the change of battery voltage is monitored to determine if the charger 20 should exit its current state. This field is provided because a test to evaluate whether or not some batteries are fully charged is the change in voltage across the battery as it is being charged. Generally, a battery evaluated under this test is considered fully charged when the voltage across the battery starts to fall, ΔVoltage goes negative.

One ΔVoltage/Δtime exit test is performed by simply monitoring the change in battery voltage. The delta voltage fields 344 associated with this test contains data indicating the drop voltage that needs to have occurred in order to satisfy the exit condition. Another ΔVoltage/Δtime exit test is performed by monitoring the change in battery voltage over time. The delta voltage field 344 integral with these exit condition test contains data indicating a slope that must be present to satisfy the exit condition.

The next two exit condition fields are used to store data related to temperature-based test conditions for evaluating whether or not the charger 20 should exit the main state for a battery being charged. A max temp field 348 stores data indicating a maximum temperature set point for the battery that would trigger the current source 110 exiting the main state.

A delta temperature field 352 stores data related to a change in battery temperature over time that would warrant the charger 20 exiting the main state. Typically, the current source 110 is triggered to exit the main state when battery temperature undergoes a relatively fast rise in temperature. For some batteries, the complementary delta temperature field 352 stores a scaler value indicating a set number of degrees of temperature. If the temperature of the battery rises above that set number of degrees in a set amount of time, the battery is considered to have satisfied that particular exit condition. For still other batteries, the delta temperature field 352 stores data representative of a temperature slope, Δtemperature/Δtime. If it is determined that the batteries temperature is rising at a rate greater than the specified slope, the battery is considered to have satisfied the test for the delta temperature exit condition.

The next data field is a display data field 358. Display data field 358 contains data that defines the information that should be presented on the display unit 30. The last data field is a load resistor data field 360. The load resistor data field 360 contains an indication of, whether during the particular state the load resistor 72 should be tied across the battery. Normally, during most battery charging states, the load resistor is disconnected from the battery. Nevertheless, as discussed above with reference to load frequency and load duty cycle fields 328 and 330, respectively, there are some charging states in which the load resistor 72 is cyclically connected to the battery. The load resistor 72 is also tied to the battery when the battery is placed in the discharge state or is the load test state.

The fields in the main state file 308 illustrated by FIG. 11, for many embodiments of the invention, are the maximum number of fields that are present in any state file 302–316. For example, it is anticipated that the wait state file 302 of most module memories 70 will only contain a current set point field 320, a minimum voltage set point field 336 and a minimum voltage next state field 338.

Similarly, there is no requirement that each main state file 308 contain each of the above fields. The main state file 308 integral with a module 26 used to charge a battery to which a constant, always-on, current is applied and that is only charged for a select time or until a battery reaches a select voltage may be smaller than the depicted main state file. Specifically, such main state file would not require the current frequency, current duty cycle, load frequency, load duty cycle data. The main state file would also not contain data about delta-voltage and temperature based exit conditions. Accordingly, the fields in which this data are stored could be eliminated.

Moreover, the data in the individual fields may vary with the files. For example, the data in the maximum temperature set point field 348 integral with a discharge state file 304 may contain data indicating the maximum temperature the load resistor 72 is allowed to reach when the battery is in the discharge state. If the signal from temperature sensor 255 indicates that the temperature of the load resistor exceeds this temperature, the charger may temporarily terminate the discharging of the battery to give the load resistor 72 the opportunity to cool to an acceptable level.

Figure 12:
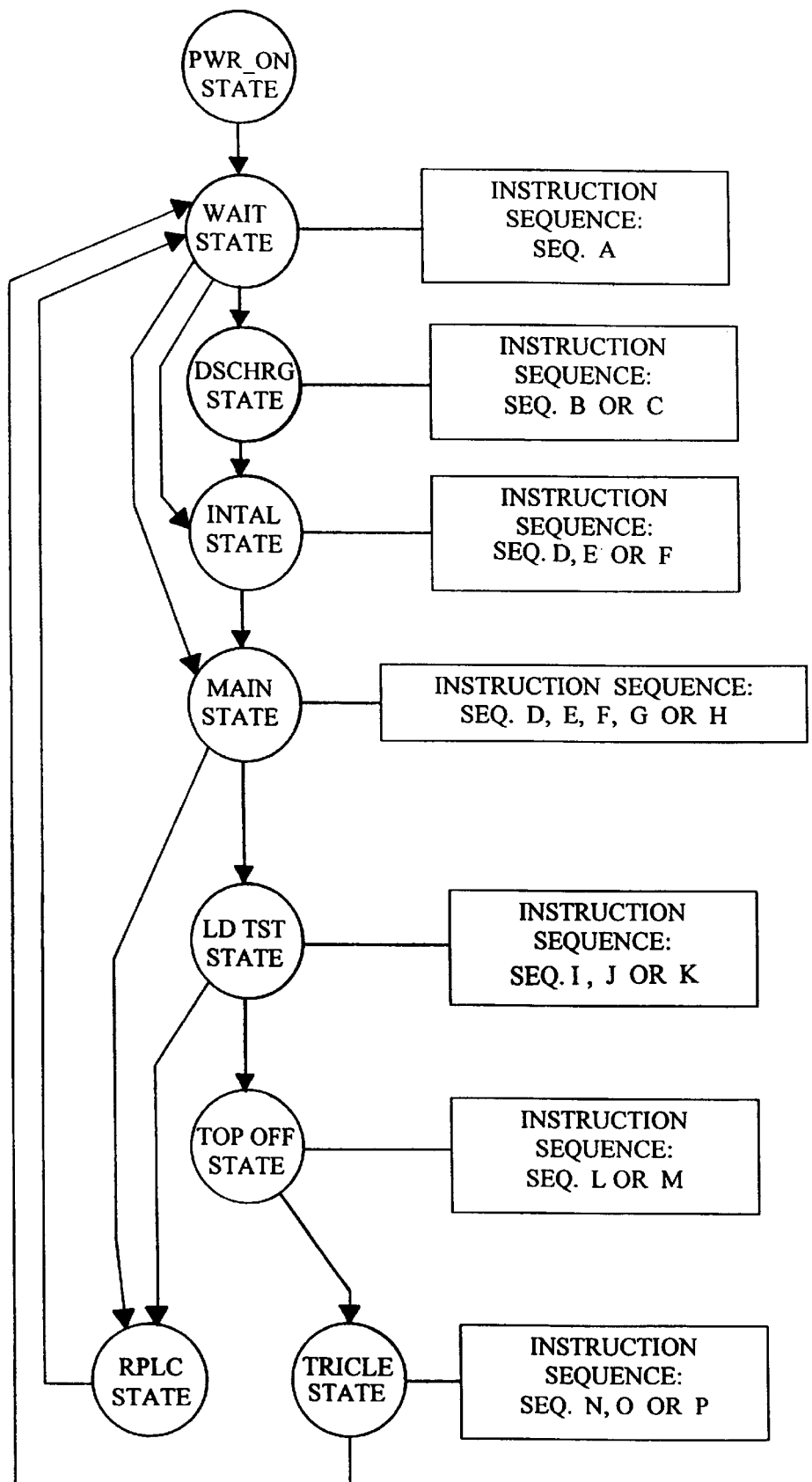
FIG. 12 is a state diagram depicting the different charging states a current source internal to the charger can be in, the transitions between the charging states and how, in each state, one of a number of instruction sequences may be executed.

The complete charging of a battery 12 is now described by reference to the state diagram of FIG. 12. In FIG. 12 the first state depicted is the power-on state for the battery charger 20. The battery charger 20 automatically enters the power-on state when it is first energized. This state, since it is initial state, does not have plural instruction sequences associated with it. Therefore, microprocessor 124 performs these processing steps automatically, without reference to the instruction set that comprises a particular instruction sequence.

In the power-on state, the microprocessor 124 first reads the data stored in each module memory 70 to determine if a module 26, 26a is, in fact, seated in each pocket 44. The connection from the BAT– terminal of the module 26, 26a to the BAT– terminal of the current source 110 effectively provides a ground reference plane for the DATAx signals that are exchanged between the microprocessor 124 and the module memory 70.

If a module is not seated in each pocket 44, microprocessor 124 causes an appropriate message to be presented on display unit 30. The microprocessor 124 may also generate CURRENT_CONTROLx signals to each of the current sources 110 to prevent any of them from generating a charging current, even if a module 26 is seated in the complementary pocket 44.

If a module 26, 26a is seated in each pocket 44, microprocessor 124 reads the state files stored in the module memory 70 and places the data contained in these files in base unit RAM 132. If the module memory 70 indicates that the battery with which the module is used contains a battery memory 282, when a batter is seated in the module 26a, the data in the battery memory 282 are also retrieved by the microprocessor 124. A single data line is used to access and retrieve data from the module memory 70 and the battery memory 282. Since the data contained in memories 70 or 282 are inherently different, one complete set of data are read in by the microprocessor 124 and stored.

Once it has been determined that there is a module 26, 26a seated in each pocket 44, microprocessor 124 sequentially reads the MEASURED_VOLTAGEx signals from each current source 110 and, if necessary the MODULE_CONTROLx signal from the associated module. Based on these signals, microprocessor asserts the appropriate control signals to the current sources 110 and modules 26, 26a. Microprocessor 124 also, at the appropriate times, performs the requisite exit conditions tests that are performed to determine when each current source 110 and battery should leave a particular charging state.

After the power-on state, each current source 110 enters the wait state. In many embodiments of the invention, it is desirable to instruct the current source 110 associated with the open-socket module 26, 26a to generate a nominal current in order to ensure the proper biasing of the components internal to the current source. The amount of this current is specified by the current set point field of the wait state file 302 stored in the memory module 70.

When the current source 110 is in the wait state, microprocessor repeatedly measures the voltage across the BAT+ terminal by measuring the voltage present on the companion MEASURED_VOLTAGEx line. As long as there is no battery seated in the socket 28, this voltage should be the open circuit voltage, 20 VDC. Once a battery is seated in the socket 28, this voltage will fall. Microprocessor 124 repeatedly compares the voltage present on the MEASURED_VOLTAGEx line to the minimum voltage specified in the minimum voltage set point field 336 of the wait state file 302. If the voltage has fallen below this level, microprocessor 124 transfers the current source 110 and complementary battery to the appropriate next state. The specific state is specified by the data in the minimum voltage next state field 338 for the wait state file 302.

In the above-described embodiment of the invention, when the current source 110 is in the wait state, two processes are repetitively executed. Specifically the current source generates a low-level current while the voltage across the BAT+ terminal is repeatedly measured. Accordingly in FIG. 12, a single instruction sequence, Instruction Sequence A, is associated with the wait state. Instruction Sequence A consists of the instructions that direct the microprocessor 124 to perform the above-described specific processes associated with the wait state.

While only one possible instruction sequence is associated with the wait state in FIG. 12 this may not always be the case. In some embodiments of the invention, it may be necessary to pulse the charging current applied to certain modules 26, 26a. In these versions of the invention, there may be second instruction sequence, not illustrated, that contains an alternative set of instructions that are executed while the current source 110 is in the wait state. These instructions would direct the microprocessor 124 to cause the current source to generate the pulse current. In these versions of the invention, the sequence identifier field 320 associated with the wait state file 302 contains data indicating which instruction sequence is executed by the microprocessor 124 when the current source enters the wait state. The wait state files 302 associated with the modules 26, 26a to which the pulsed current is applied contain current frequency and duty cycle fields 324 and 326, respectively. These fields 324 and 326 contain the data describing the frequency with which the pulsed current should be supplied to the open socket module 26.

One possible next state the battery and associated charge components enters after exiting the wait state is the discharge state. In the discharge state, the battery is tied across the load resistor 72 before the actually charging is initiated. The current set point field 323, if contained with the discharge state file 304, indicates the current source 110 is set to not apply a charging current to the battery.

The sequence identifier field 322 associated with the discharge state file 304 indicates which one of two instruction sequences, Instruction Sequence B or C, contains the instructions describing how the specific battery is to be discharged. If a battery is to be continually discharged by the load resistor 72, the sequence identifier field 322 contains data indicating the instructions within Instruction Sequence B are to be executed. These instructions direct the microprocessor 124 to simply continually tie load resistor 72 across the battery.

Alternatively, it the battery is to be pulse discharged, sequence identifier field 322 contains data indicating that the Instruction Sequence C instructors are to be executed. If battery is so discharged, the associated memory module discharge state file 304 contains load frequency and load duty cycle fields 328 and 330. The associated load resistor data field 360 contains an indication that the load resistor 72 is to be cyclically tied across the battery.

In one version of the invention, the sole exit condition upon which a current source 110 exits the discharge state is the battery voltage falling below a specified level. For each battery, this voltage level is specified in the minimum voltage set point field 336 integral with the discharge state file 304.

Nevertheless, it should be recognized that it may be possible to configure the battery charger 20 so that in other versions of the discharge state, the battery will exit the state based on other exit conditions occurring. For example, some batteries are only discharged for a select amount of time before they are considered to complete the discharge step. The complementary module memories 70 contain data in their discharge state file sequence identifier fields 322 pointing to a different instruction sequence not depicted in FIG. 12. This instruction sequence contains instructions for time-dependent battery discharging. The discharge state files 304 of the module memories 70 associated with these batteries contain maximum time set points fields 342. These fields 342 contain data that indicate how long the associated batteries should be discharged before they exit the discharge state. The charger 20 discharges these batteries based on the instruction sequence instructions that comprising this instruction sequence. The amount of time each of these batteries is discharged is based on the data contained in the time set point fields 342.

For many batteries, the first current charging state is the initial state. Current is supplied in accordance with the instructions that comprise one of three instruction sequences, Instruction Sequences D, E or F. In the depicted example, a battery charged by the instructions comprising Instruction Sequences D or E is supplied with a constant current. A battery charged according to the instructions that comprise Instruction Sequence F is supplied with a pulsed current. The actual characteristics of the current supplied are based on the data contained in the initial state file 306 of the memory module 70 with which a battery is associated.

The actual process steps, and the sequence in which those steps are executed, by the charger during the initial state, as well the other states, is a function of which set of instructions are executed when the battery enters that particular state. For example, a battery may be designed to be supplied with a charging current until it reaches a selected minimum voltage before it is allowed to enter the main state charging. For this type of battery, the data within the sequence identifier field 322 for the initial state file 306 associated with the complementary module memory 70 instructs the microprocessor 124 to cycle the current source 110 through the instructions that comprise Instruction Sequence D.

Figure 13:
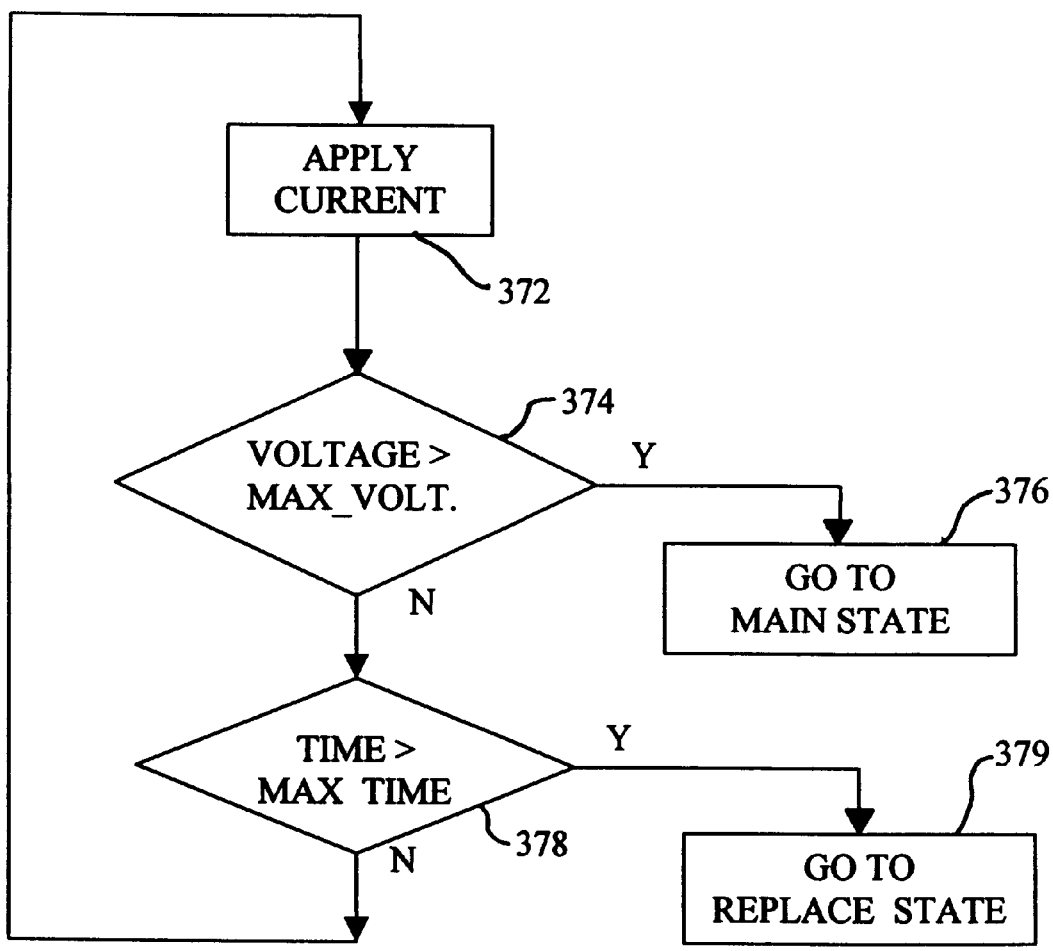
FIG. 13 is a process diagram illustrating the process steps that form one instruction sequence through which the charger of this invention can cycle.

The process steps executed by the charger 20 as it cycles through Instruction Sequence D instructions are now illustrated by FIG. 13. In this charging state, the constant charging current is applied to the battery, as represented by step 372, based on the current set point field 323 data for the initial state file 306. Then, in step 374, the voltage from the MEASURED_VOLTAGEx line is compared to the maximum voltage specified by the associated maximum voltage set point field 332. If the voltage exceeds the specified maximum voltage, the battery and associated charger components enter the appropriate version of the main state, step 376. The indication that the battery should now enter the main state comes from the data contained in the maximum voltage next state field 334.

If, however, the battery voltage is below the maximum voltage, microprocessor 124, in step 378 determines if the battery has been in the initial state for more than the maximum time as specified by the maximum time set point field 340. If the battery has been charged for less than the maximum time, the charger 20 continues to charge the battery as represented by the loop back to charging step 372.

However, collectively, in steps 374 and 378 it may be determined that the battery voltage has remained below the maximum voltage level for greater than the maximum allotted time. If this determination is made, it is assumed that the battery can no longer hold a charge and needs to be replaced. Accordingly, the complementary maximum time next state field 342 contains data indicating that the current source 110 and battery are to enter the replace state. Therefor, as represented by step 379, the battery enters the replace state. (To minimize the complexity of FIG. 12, this transition and many of the other transitions to the replace state are not illustrated).

Figure 14:
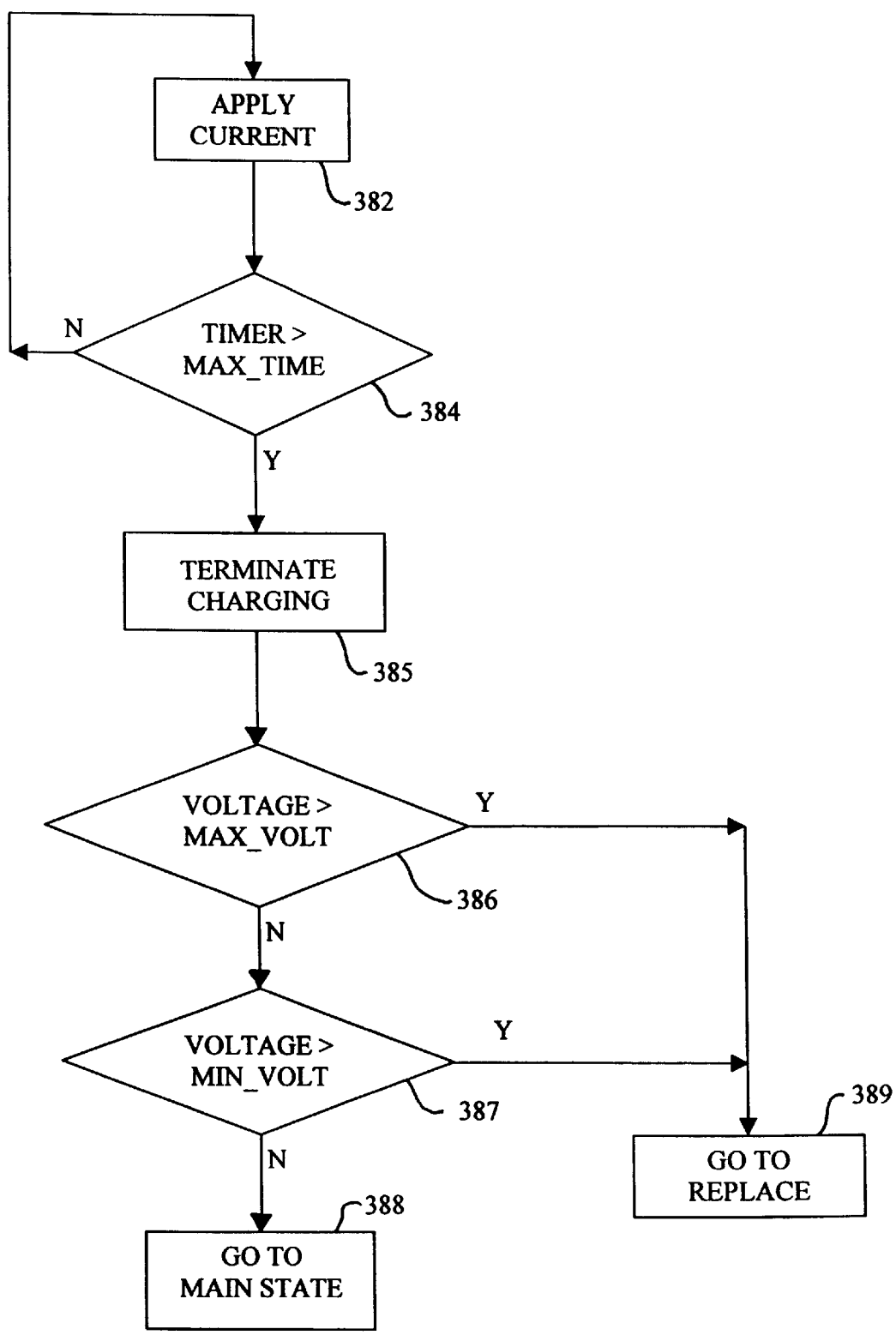
FIG. 14 is a process diagram illustrating the process steps that form a second instruction sequence through which the charger of this invention can cycle.

Alternatively, a battery may subjected to initial state charging for a select amount of time. At the end of this time period, the voltage of the battery is tested. If the voltage is within a select range, the battery is allowed to enter the main state for further charging. A battery charged according to this sequence of steps is charged according to the instructions that comprise Instruction Sequence E, now described with respect to FIG. 14. In this sequence, the battery is supplied with a charging current in a step 382 which is functionally similar to charging step 372. As represented by step 384, microprocessor 124 constantly compares the time the battery has been in the initial state to the maximum time. If the overall time the battery has been in the initial state is less then the maximum time, the current source 110 continues to charge the battery as represented by the loop back to step 382.

Once the battery has been charged for the maximum time, the charging ceases, step 385. Then, as represented by steps 386 and 387, respectively, the voltage across the battery is compared to the maximum and minimum voltages. These are the set point voltages obtained from fields 332 and 336, respectively, from the initial state field 304 internal to the memory module 70 with which the battery is associated. If the measured voltage is between the specified minimum and maximum voltages, the battery exits the initial state and enters the main state, step 388. Here, the maximum time next state field 342 contains the data which indicates the that the battery should enter the main state.

If, however, the battery voltage is outside of the range defined by the minimum and maximum voltage set points, the battery is considered defective. Based on data contained in the next state fields 334 and 338, the battery enters the replace state, step 389.

Returning to FIG. 12, it can be seen when the battery is in the main state, its charging is based on the instructions in one of five different sequences, Instruction Sequences D, E, F, G or H. Instruction Sequences D, E and F are the instruction sets described above through which the current source 110 could potentially cycle while in the initial state. The depiction of these instruction sequences in association with the main state should be recognized as a another aspect of this invention; an instruction sequence through which the charger 20 cycles may be repetitively executed during the charging of a single battery.

Instruction Sequences G and H comprise additional sets of instructions that may be executed during main state charging of a battery 22. Instruction Sequence G consists of instructions that are executed during a pulsed-charge version of the instructions that comprise previously described Instruction Sequence D. Instruction Sequence H consists of the instructions executed to charge a battery that include the steps of periodically tieing the battery to the load resistor 72 and waiting for either a voltage or temperature based exit condition to occur.

Unless it is determined that a battery needs to be replaced, a current source 110 and battery exit the main state and typically enter a load test state. In the load test state, the battery is no longer supplied with a charging current. The GATEx signal is asserted so as to tie the load resistor 72 across the battery. The voltage across the load resistor 72 is measured by monitoring the voltage of the signal present on the MEASURED_VOLTAGEx line. This voltage measurement is then used as a basis for determining the watt-hours of power stored in the battery. As discussed hereinafter, if the battery has a temperature sensor 286, battery temperature is also employed as a variable for determining stored energy.

Once this determination of stored energy is made, this information is presented on the display unit 30. In one particular version of the invention, the LCD display 32 includes four bar graphs; one bar graph is associated with each module 26. The presentation of battery stored energy is made by illuminating the bar graph to a height that represents the stored energy in proportion to the energy stored in a new battery. Also, one of the LEDs in array 34 may be illuminated to indicate that the battery is ready for use. The data in the display field 360 of the load test file 310 contain the instructions for actuating the display 30.

In FIG. 12, Instruction Sequences I, J and K are shown as containing the three instruction sets through which the current source 110 may cycle during the load test state. Instruction Sequence I contains the instructions that continually tie the battery 22 to the load resistor 72. Instruction Sequence J contains the instructions that are executed to cyclically tie the battery to the load resistor 72. The third set of instructions, the instructions of Instruction Sequence K, are the instructions executed to test a battery with an internal temperature sensor 286 and battery memory 282 as described hereinafter.

The sequence identification field 320 integral with the load test state file 310 contains data indicating which Instruction Sequence I, J or K is to be execute for the battery associated with that file. The load test file 310 also contains data indicating the total time the load resistor 72 should be tied to the battery. If the battery is load tested according to the processes specified by Instruction Sequence J, the load test state file 310 contains data fields indicating the rate and total time at which the load test resistor should be cyclically tied to the time period for which it should be constantly tied to the battery.

During the load test state, the microprocessor 124 tests the voltage across the load resistor 72 to determine if it meets a certain minimum level specified in the load test state file 310. If the test voltage exceeds this level, the current source 110 and battery typically enter the trickle state. If the test voltage does not rise to the minimum level, the current source 110 and battery enter the replace state.

Normally, immediately after the load test state, the microprocessor 124 has the current source 110 enter the top off state. When the current source is in the top off state, a small, fixed amount of current is applied to the battery to replace the charge lost during the load test state testing. In FIG. 12, the current source 110 is shown as cycling through the instructions that comprise either Instruction Sequence L or Instruction Sequence M when in the load test state. Instruction Sequence L contains the instructions that are executed to cause the constant current toping off of the battery. Instruction Sequence M contains the instructions that are executed to apply a pulsed current during the top off state.

Typically, the exit condition test for evaluating whether or not a current source 110 should exit the top off state is the overall time it is in that state. Voltage tests may be performed at the end of the toping off process to again determine if a fault has occurred which would dictate having the battery enter the replace state. These specific exit condition test is one of the instructions comprising Instruction Sequences L and M.

After a battery is topped off, the current source 110 and battery enter the trickle state. While in the trickle state, the current source 110 applies a very small charge to the battery to prevent it from losing its charge. The charging of the battery when in this state is based on one of three sets of instructions that form Instruction Sequences N, O or P.

Once a battery is removed from a module 26, the module is consider to have exited the trickle state. When the battery is in the trickle state, the evaluation of whether or not this exit has occurred is made by monitoring the voltage across the battery. A rise in voltage above a maximum voltage set point is interpreted as an indicated that the battery has been pulled from the module 26 and the socket 28 is now open. In response to this exit condition occurring, microprocessor 124 returns the current source 110 to the wait state.

FIG. 12 also depicts the replace state. The replace state is the state in which the battery defaults if a particular exit condition test has indicated that the battery is not able to hold a charge. The display data field 358 integral with the replace state file 316 of the memory module 70 indicates what type of information display unit 30 should present about the failure of the battery. Typically, one LED of array 34 is illuminated to provide an indication that the battery needs to be replaced. In some embodiments of the invention, the replace state file 316 will contain multiple data fields 358 with different information display instructions. Microprocessor 124 will then display information based on the data held in one of the fields 358 based on the particular battery failure that caused the battery to enter the replace state.

Generally, the exit conditions that cause a battery to exit the trickle state are the exit conditions that must be present to cause the battery to exit the replace state. When the battery is removed during the replace state, the associated current source 110 returns to the wait state.

Figure 15:
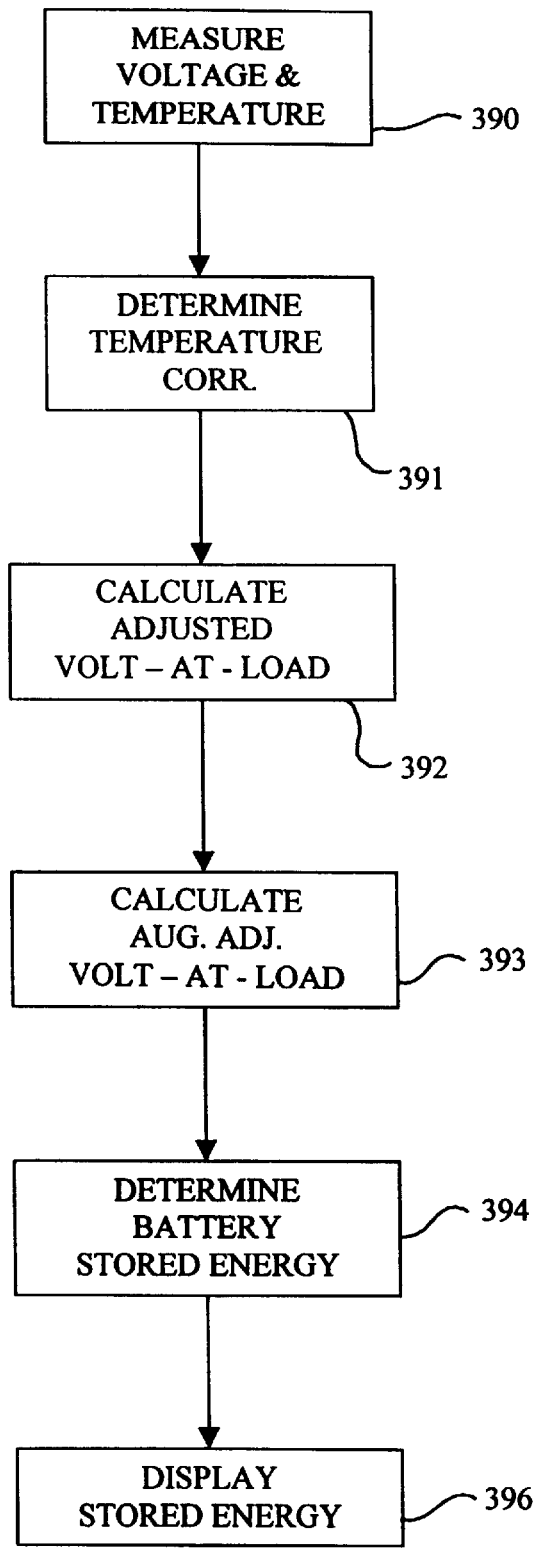
FIG. 15 is a process diagram illustrating how the charger of this invention can calculate the stored energy of a battery the charger has been employed to charge.

If a battery has an internal memory 282 and temperature sensor 286, during the load test state, the battery charger 20 of provides a relatively accurate measurement of stored watt hours of energy in the battery. Specifically, when the battery has a temperature sensor, for example, sensor 286 of battery 20, charger 20 performs the stored watt hour calculation as a multi-step process. These steps, which are illustrated in FIG. 15, are the instructions that partially comprise the above-described Instruction Sequence K (FIG. 12). Initially, in step 390, the charger 20 measures the voltage at load, the voltage across the load resistor 72, and determines what the temperature of the battery based on the data provided by the sensor 283.

Figure 16:
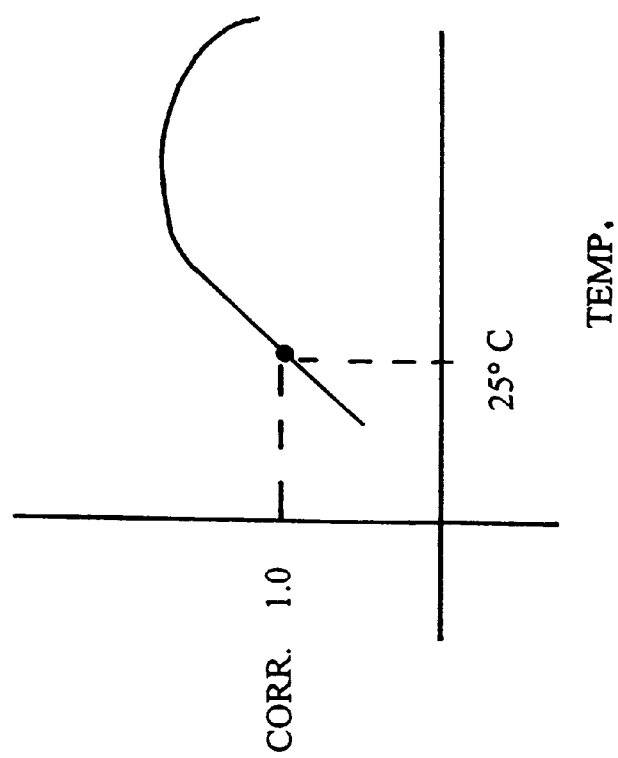
FIG. 16 is a graph depicting the relationship between a voltage-at-load:adjusted-voltage-at-load coefficient and battery temperature.

Then, based on the foregoing voltage and temperature variables, the charger 20 determines an adjusted voltage-at-load value for the battery. As seen by reference to the graph of FIG. 16, empirical data makes it possible to determine how the temperature of a battery causes its voltage-at-load to vary. In the depicted graph, this variation is depicted as a deviation from a 1.0 correlation between the measured voltage-at-load and a reference voltage-at-load. The module memory 70 associated with a battery contains a voltage adjust file 317 (FIG. 10) in which data representative of this curve for the battery are stored. Accordingly, microprocessor 124 determines the correlation between the measured and adjusted voltage based on the measured battery temperature, step 391. The microprocessor 124 then produces an adjusted voltage-at-load value, step 392.

Figure 18:
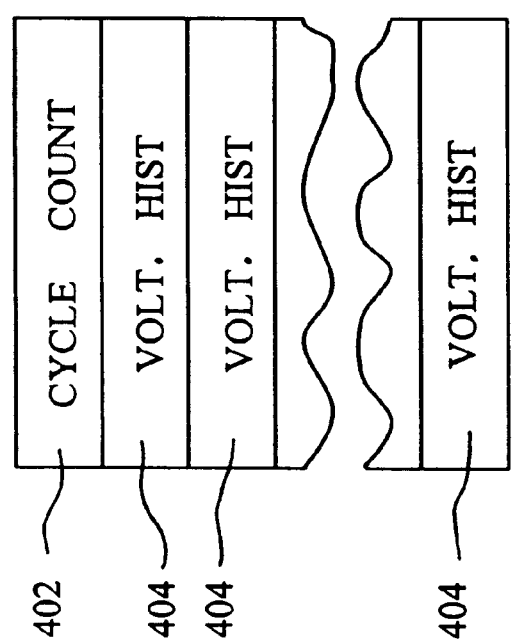
FIG. 18 represents the data fields within the memory of a battery.

As discussed below, battery memory 282 contains voltage history fields 404 (FIG. 18). The previously calculated adjusted voltage-at load values for the battery 22 are stored in these fields 404. When the charger 20 calculates the stored energy held in batteries 22 having these memories 282, the next step, step 393, is the calculation of the average voltage-at-load. This average voltage-at-load is calculated by calculating an average based on the previously calculated adjusted voltage-at-load value from step 392 and the previously calculated, stored adjusted voltage-at-load values stored in the battery memory 282. The formula employed to make this calculation may provide a weighted average value that is based more on the last-calculated adjusted voltage-at-load value or on the stored adjusted-voltage-at-load values. Once this average voltage-at-load value is calculated, the stored energy calculation proceeds to step 394.

Figure 17:
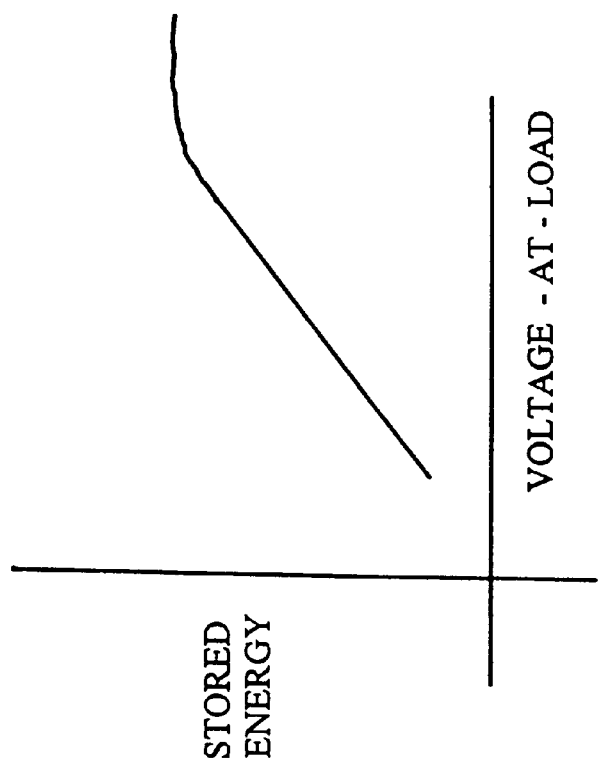
FIG. 17 is a graph depicting the relationship between the voltage-at-load for a battery and the stored watt-hours of charge within the battery.

In step 394, the stored energy of the battery 22 is determined. This determination is made by reference to the voltage-at-load to stored watt-hours curve represented by FIG. 17. The data representative of this curve for a specific battery is stored in the stored volts/energy file 318 (FIG. 10) of the module memory 70.

If a battery only has a temperature sensor 286, but no memory for storing previously calculated adjusted voltage-at-load values, the execution of step 393 is omitted. When the charger 20 is used with these batteries, the determination of stored energy is made using the adjusted voltage-at-load value calculated in step 392 as the reference voltage for determining stored energy in step 394.

If a battery does not have a temperature sensor, microprocessor 124 simply determines the stored watt-hours by reference to the measured voltage across the load resistor 72 and the data in the stored volts/energy file 318.

Once the stored energy is calculated, this value is presented on display unit 30, step 396. In the depicted version of the invention, the display process includes an initial step of determining the percentage of stored energy in the battery in comparison to the stored energy a new, fully-charged battery could hold. This step is performed by dividing the calculated stored energy for the battery by a value representative of the stored energy a new battery can hold. This latter data is retrieved from a field internal to the volts/energy file 318 internal to the module memory 70, (field not illustrated.)

Once this percentage calculation is executed, step 396 proceeds with the presentation of this percent data on the display unit 30. Specifically, the bar graph integral with LCD display 32 is illuminated to provide the user with an indication of the extent to which the charge in the battery measures up to the charge held in a new battery. Indices presented by the LCD display 32 around the bar graph make it easy for the personnel using the charger 20 to quickly determine the relative quantity of energy stored in the battery.

When the battery 22 is charged with charger 20, the charger reads and writes to the battery memory 282, the contents of which are now described by reference to FIG. 18. Specifically, battery memory 282 has a verification code field 401. Data comprising a verification code are stored in field 401. This verification code is the code that is checked when the battery 22 is initially coupled to the module to verify that the battery is intended for use with that module. There is also a cycle count field 402. This field is used to store data indicating how many times the battery has been charged. During the load test state, for example the load test state, microprocessor 124 will read the contents of the cycle count field and rewrite the data in this field to update the count. It is assumed that prior to each charging of a battery, the battery is sterilized. Accordingly the data in the cycle count field 402 is assumed to provide an accurate indication of how many times the battery has been sterilized. This count is the cycle count that is presented on the LCD 32 during the charging of the battery.

Battery memory 282 also has a set of voltage history fields 404. Each voltage history field 404 is written to once during the lifetime of the battery by microprocessor 124 to indicate the adjusted voltage-at-load of the battery after it has been subjected to a particular number of charging cycles. For example, one version of battery memory 282 may have sufficient voltage history fields 404 so that the microprocessor can indicate the adjusted voltage-at-load of the battery after the fifth, tenth, fifteenth, twentieth, etc charging cycle. In some versions of the invention, this data is stored in a compressed formate to minimize the size of the individual fields. It should, be recognized that compressed data may only represent an approximation of the adjusted voltage-at-load values that were previously calculated.

Figure 19:
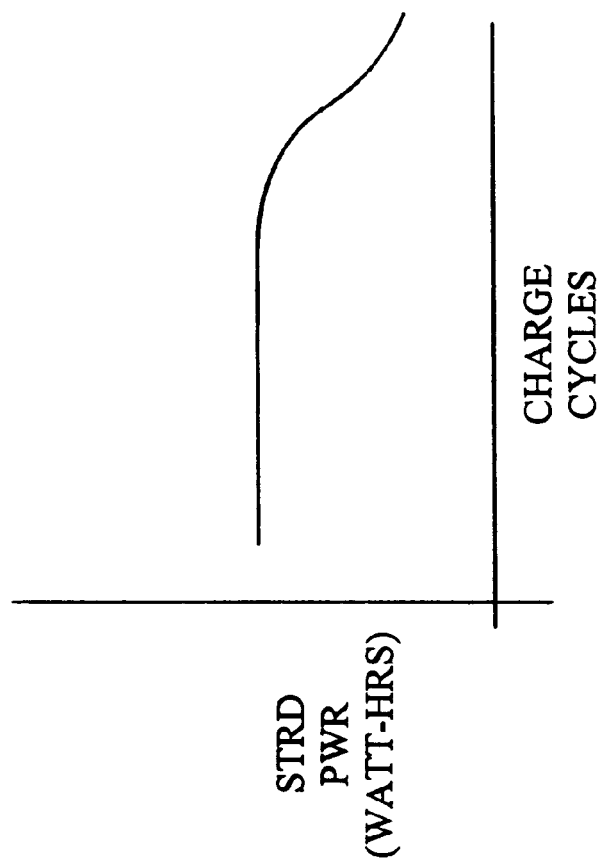
FIG. 19 is a graph representative of the relationship between of the charge/sterilization cycles of the battery and the expected stored watt-hours of power within the battery.

The data in voltage history fields 404 are the data employed by the charger to determine average voltage-at-load in the above described step 393 of the stored energy calculation process. The data in voltage history fields 404 is also available for studied by maintenance technicians to evaluate the usage pattern of the battery After battery 22 has been load tested and its stored watt-hours calculated, microprocessor 124 evaluates if the battery is performing within acceptable operating parameters. This determination is made by determining how the stored watt-hours for the battery compares to an expected minimum stored watt-hours for that battery based on the number of times it has been charged (sterilized). The memory module 70 associated with the battery contains a minimum watt-hours file 319 (FIG. 10) representative of the watt-hours/usage curve of FIG. 19. As seen in FIG. 19, the minimum number of watt hours of energy the battery 22 should be able to store is a function of the number of times the battery has been properly sterilized.

Microprocessor 124 determines the current minimum stored watt-hours for battery 22 based on the data in file 319 and the retrieved data from field 402 indicating the number of times the battery has been charged (sterilized). If the stored watt-hours of energy is below the expected minimum, microprocessor 124 presents this information on display unit 30. This information may, for example, be displayed by cycling one of the LEDs of array 34 on and off. The display of this information provides the personnel charged with sterilizing the battery 22 that it may be necessary to revise their sterilization procedures so as to minimize the excessive reduction of battery utility.

The battery charger 20 of this invention provides a relatively wide range of utility. The microprocessor 124 controls the charging of the individual batteries so that each battery can be independently cycled through different charging states. Moreover, the instruction sequence that is executed when the battery is in a particular charging state can be varied on a battery-by-battery basis. Thus, if the charging of two batteries vary by only the sequence of execution of several process steps, both batteries can be still be charged by this charger. Still another feature of this charger is that each of the modules 26, 26*a* is provided with socket 28, 28*a* especially intended to receive the batteries with which the modules are associated.

Collectively, these features make it possible to use the charger of this invention with a wide number of batteries that have different shapes or that are subjected to different charging processes. This utility serves to reduce the number of chargers a facility has to have on site if it has different numbers of batteries.

The charger of this invention also does more than provide an indication of whether or not a battery is ready for use. The charger provides information about the energy stored in a fully charged battery. In the described version of the invention, this information as presented as an indication of the stored energy relative to the energy that can be stored in a new battery. This data is very useful in a surgical situation. For example, if a battery is near the end of its useful life, while fully charged, the quantity of energy it holds may not be sufficient for it to power a tool for a particular surgical procedure. This information is presented on the display 30 as indication that the battery's stored energy is significantly less than that of a new battery. Accordingly, the surgical personnel would know that they should use a newer battery to energize the tool for that procedure.

Also, if a battery with which this charger 20 is used has a temperature sensor 286, the charger provides a temperature-adjusted measure of the stored watt-hours of the battery. This measure of stored energy provides a significantly more accurate measure of the utility of the battery than a measure based on voltage-at-load alone. This feature compensates for the fact that if the battery is charged after it is removed form the autoclave, it may be at an elevated temperature.

If the charger 20 is used with the battery 22 of this invention, collectively these components provide even more useful information about the battery. Specifically, the stored watt-hours calculation can then be based on the average, adjusted voltage-at-load. This provides for an even more accurate means of determining the stored energy of the battery. Moreover, the charge cycle data and voltage-at-load data held be the battery make it possible to determine if, over its lifetime, the battery is performing as expected. If the battery is not performing properly, the persons charged with sterilizing it can evaluate if it is necessary to revise their sterilization procedures.

It should be recognized that the foregoing description is limited to one particular embodiment of this invention. It will be apparent that variations can be made to this invention with the attainment of some or all the advantages thereof. Clearly, the circuitry employed in the base unit can vary from what has been described. Also, in some versions of the invention, the memory internal to the battery may contain the state files 302–316 indicating the states and instruction sequences through which the battery is cycled during charging. This battery-stored data can be employed as override data that substitutes from the instruction-containing data in the module memory 70. Microprocessor 124 upon reading the battery-stored data, determines which instruction-containing data, the data is the module memory 70 or the data in the battery memory 282, are to be used to control the charging of the battery. Also, data describing the instruction sequences of the batteries may be presented in formats different from what has been described.

It should likewise be recognized that not all versions of this invention may be equipped with four modules. Some versions of the invention may be able to charge only one, two or three batteries at a time. Other versions of the invention may be able to charge more than four batteries simultaneously.

Also, it should be understood that the various charging states are meant to be only an exemplary embodiment of the invention. For example, other embodiments of the invention may have more or less charging states and more or less versions of each state. For example, as is illustrated in FIG. 12, the charging of some batteries may progress from the wait state directly to the initial state or the main state.

Also, it should be understood that the order in which a battery enters and exits particular states may vary from what has been described. A battery may, for example have to cycle through two main states; one at medium current and a second one at a higher current. In order to perform this charging, the appropriate next state field of the first main state file would contain an indication that battery is to enter the second main state. The second main state file contains data in its sequence identifier field 320 indicating the instruction sequence that is to be executed in order to complete the main state charging of the battery. This instruction sequence may be identical to the just-executed instruction sequence.

Similarly, some batteries may not be trickle charged.

Also, in the described version of the invention each state file 302–316 contains only one sequence identifier field 320. In alternative versions of the invention, each state file may contain plural instruction fields. Each of these instruction fields contains data that identifies a specific process that is to be performed by the charger when the battery is in the associated state. Collectively, the instruction fields would contain data that identify the sequence of instructions that are to be executed by the charger 20 during a particular charging state of the battery. Data fields 322–360 would still contain data describing the parameters of the charging current and the exit condition tests associated with the individual process steps.

Thus, in this version of the invention, each module memory 70 would contain data that describes on a step-by-step basis the process steps that the charger 20 is to execute in order to charge the associated battery. This version of the invention offers provides an even more specific means on a battery-by-battery basis to control the charging of the individual batteries.

It should likewise be recognized that all the possible battery charging and exit condition test sequences have not been described. For example, if the voltage across the battery is measured as a voltage across an on-module board 68 voltage divider, still other sequences may be required. The same is true if, for other charging cycles it is necessary to measure battery temperature or temperature of the load resistor 72. Also, derivatives of voltage and/or temperature measurements may be parameters that are tested to determine if a battery should exit a particular charging state. Moreover, an instruction sequence may include plural exit condition tests based on the same parameter. For example, an instruction sequence may include exit condition tests that are based on both absolute voltage and temperature values as well as tests that are based on the derivatives of these values.

Also, it should be understood that the next-state destination of plural exit condition tests may very well be the next state in the normal progression of the charging of the battery. For example some batteries may be configured to proceed from main state charging to load testing whenever the voltage across the battery rises to a selected level, there is a drop in voltage across the battery or the battery is subjected to the main state charging current for a select amount of time. The instruction sequence integral with this main state charging of the battery contains instructions indicating that the battery should be subjected to each of these exit condition tests. The next state fields in the main state file 308 associated with these tests for that battery each contain data indicating that the next state for this battery is the load test state.

Moreover, it may be desirable to provide voltage-regulated charging of the battery instead of or in combination with the above described current-controlled charging. The state fields associated with the instruction sequences in which there is voltage-regulated charging would include data indicating the target voltage on which this charging should be based.

Alternative means may be employed for measuring the stored energy of some batteries. For example, it may be desirable to apply a current to a particular battery and to then use this current as a means for measuring the impedance of the battery. The battery impedance is, in turn used as input variable upon which the stored energy of the battery is determined.

Also, not all features may be provided with all versions of this invention. Some versions of the invention, for example, may not have the system for providing an indication that the ability of a battery to store charge is below what was expected. Therefore, it is an object of the appended claims to cover all such variations and modifications that come within the true spirit and scope of this invention.

What is claimed is:

1. A method for evaluating the quantity of energy stored in a charged battery, said method comprising the steps of:

tieing opposed terminals of the battery across a load resistor and measuring the voltage across the load resistor to produce a measured voltage-at-load of the battery;

measuring the temperature of the battery;

determining a temperature coefficient based on the temperature of the battery and a first set of reference data;

determining an adjusted voltage-at-load based on the measured voltage-at-load and the temperature coefficient; and determining the stored energy in the battery based on the adjusted voltage-at-load and a second set of reference data.

2. The method for evaluating the stored energy of a battery of claim 1, wherein, after said step of determining the adjusted voltage-at-load, data representative of the adjusted voltage-at-load is stored in a memory integral with the battery as historical voltage-at-load data.

3. The method for evaluating the stored energy of a battery of claim 2, wherein:

the historical voltage-at-load data in the battery memory are read;

after said determination of the adjusted voltage-at-load, an average voltage-at-load value is calculated based on the adjusted voltage-at-load and the historical voltage-at-load data; and said determination of stored energy is performed based on the average voltage-at-load and the second set of reference data.

4. The method for evaluating the stored energy of a battery of claim 1, further including the steps of:

calculating a battery utility rating based on the determined stored energy and a fixed energy value; and presenting an indication of the battery utility rating on a display.

5. The method for evaluating the stored energy of a battery of claim 4, wherein the fixed energy value is a measure of the energy a new battery can store.

6. The method for evaluating the stored energy of a battery of claim 1, wherein said step of measuring the temperature of the battery is performed by monitoring the signal from a temperature sensor that is located inside the battery.

7. A method of charging a battery, said method comprising the steps of:

applying a charging current to the battery;

after said step of applying the charging current to the battery is completed, connecting opposed terminals of the battery across a load resistor;

measuring the voltage across the load resistor to produce a measured voltage-at-load for the battery;

determining the temperature of the battery;

determining the stored energy in the battery based on the measured voltage-at-load and the temperature of the battery; and displaying an indication of the stored energy in the battery.

8. The method of charging a battery of claim 7, wherein said step of determining the stored energy in the battery is performed by:

determining an adjusted voltage-at-load for the battery based on the measured voltage-at-load and the temperature of the battery; and determining the stored energy in the battery based on the adjusted voltage-at-load.

9. The method of charging a battery of claim 8, wherein:

said step of applying a charging current to the battery is performed by a current source located within a battery charger;

the battery charger includes a processor for performing said step of determining the adjusted voltage-at-load for the battery and said step of determining the stored energy in the battery;

said step of determining the adjusted voltage-at-load for the battery is performed based on a first set of reference data that is stored in a portable memory that is removably attached to the battery charger, wherein, when the portable memory is attached to the battery charger, the processor reads the data in the portable memory; and said step of determining the stored energy in the battery is performed based on a second set of reference data that is stored in the portable memory and that is read by the processor.

10. The method of charging a battery of claim 7, wherein:

said step of applying a charging current to the battery is performed by a current source located within a battery charger;

the battery charger includes a processor for performing said step of determining the stored energy of the battery; and said step of determining the stored energy in the battery is performed by the processor based on reference data that is stored in a portable memory that is removably attached to the battery charger, wherein, after the portable memory is attached to the battery charger, the processor reads the reference data from the portable memory.

11. The method of charging a battery of claim 10, wherein:

prior to said step of applying charging current to the battery, the battery is placed in a module that is removably attached to the battery charger; and the portable memory in which the reference data are stored is attached to the module and the processor reads the reference data from the portable memory after the module is attached to the battery charger.

12. The method of charging a battery of claim 10, wherein, the portable memory in which the reference data are stored is mounted in the battery and, after the battery is coupled to the battery charger, the processor reads the reference data from the portable memory.

13. The method of charging a battery of claim 7, wherein:

after said step of measuring the voltage-at-load for the battery is performed, an adjusted voltage-at-load is calculated based on the measured voltage-at-load and the temperature of the battery;

data representative of the adjusted voltage-at-load is stored in a memory integral with the battery as historical voltage-at-load data;

after a subsequent charging of the battery, after said step of calculating the adjusted voltage-at-load is executed, an average voltage-at-load is calculated based on the adjusted voltage-at-load and the historical voltage-at-load data; and said step of determining the stored energy in the battery is performed based on the calculated average voltage-at-load.

14. The method of charging a battery of claim 7, wherein:

after said step of determining the stored energy in the battery is executed, battery utility is calculated based on the determined stored energy and a fixed energy value; and in said step of displaying an indication of the stored energy in the battery, the calculated battery utility is displayed.

15. A charger for providing energization current to a battery, said charger having:

a base unit having a display;

a current source disposed in said base unit configured to be connected to the battery for supplying a charging current to the battery;

a load resistor and a switch, said switch being connected to the battery and said load resistor for selectively connecting the battery across said load resistor; and a processor unit disposed in said base unit, said processor unit being connected to:

said current source for regulating the application of current by said current source to the battery;

said switch for selectively actuating said switch to selectively tie the battery across said load resistor;

a temperature sensor associated with the battery;

said load resistor for receiving a signal representative of the voltage across the load resistor; and to said display, and said processor unit: actuates said switch to tie the battery across said load resistor; receives from the load resistor a signal representative of the voltage across the load resistor; receives from the temperature sensor a signal representative of the temperature of the battery; determines the stored energy of the battery based on the voltage across said load resistor and the temperature of the battery; and causes said display to present an indication of the stored energy of the battery.

16. The battery charger of claim 15, wherein, said processor unit:
calculates an adjusted voltage-at-load for the battery based on the voltage across the load resistor and the temperature of the battery; and
determines the stored energy of the battery based on the adjusted-voltage-at-load of the battery.

17. The battery charger of claim 16, wherein:
said base unit further includes a connector for releasably receiving a memory that is associated with the battery;
said processor unit is connected to the battery memory through said connector for reading data from the memory and is further configured to calculate the adjusted voltage-at-load for the battery based on data read from the memory and to determine the stored energy of the battery based on data read from the memory.

18. The battery charger of claim 16, wherein:
said base unit further includes a connector for releasably receiving a memory that is integral with the battery;
said processor unit is connected to the battery memory through said connector for writing data into and reading data from the memory and is further configured to: write into the battery memory data representative of the adjusted voltage-at-load for the battery as historical voltage-at-load data; read from the battery the historical voltage-at-load data; calculate an average voltage-at-load for the battery based on an immediately preceding adjusted voltage-at-load determined for the battery and the historical voltage-at-load data; and determine the stored energy of the battery based on the average voltage-at-load.

19. The battery charger of claim 15, wherein:
said base unit is formed with an opening for releasably receiving a module, said module having a socket for receiving the battery and conductors through which current from said current source is applied to the battery;
a memory is attached to said module, said memory containing reference data; and
said processor unit is connected to said module memory for reading the reference data and is configured to determine the stored energy of the battery based on the voltage across said load resistor, the temperature of the battery and the reference data read from said module memory.

20. The battery charger of claim 19, wherein said load resistor is secured to said module.

21. A charger for charging a rechargeable battery, said charger including:
a base unit, said base unit having a socket for receiving the battery;
a current source disposed in said base unit for applying a charging current to the battery; and
a processor disposed in said base unit, said processor being connected to:
said current source;
a load resistor and a switch that selectively connects the battery across the load resistor;
a temperature sensor that monitors the temperature of the battery; and
a memory that is removably attached to said base unit, said memory storing reference data, and said processor:
reads the reference data in the memory;
controls said current source to regulate the charging of the battery by said current source;
selectively actuates the switch to selectively tie the battery across the load resistor;
determines from the load resistor a measured voltage-at-load for the battery;
determines an adjusted voltage-at-load for the battery based on the measured voltage-at-load, the temperature of the battery as indicated by the temperature sensor and the reference data read from the memory; and
determines the stored energy of the battery based on the adjusted voltage-at-load for the battery and the reference data read from the memory.

22. The charger of claim 21, wherein the socket is part of a module that is removably attached to said base unit and said memory in which the reference data are stored is attached to said module.

23. The charger of claim 21, wherein the socket is part of a module that is removably attached to said base unit and said load resistor is attached to said module.

24. The charger of claim 21, wherein:
a memory is integrally associated with the battery; and
said processor is configured to write data to and read data from the battery memory and said processor determines the stored energy of the battery by: writing into the battery memory data representative of the adjusted voltage-at-load for the battery as historical voltage-at-load data; after an adjusted-voltage-at-load determination is made, calculating an average voltage-at-load for the battery based on the adjusted voltage-at-load and historical voltage-at-load data read from the battery memory; and determining the stored energy of the battery based on the average voltage-at-load and the reference data.

25. The charger of claim 24, wherein the reference data are stored in the battery memory and said processor is configured to read the reference data from the battery memory.

26. The charger of claim 21, wherein the battery has a memory integrally associated with the battery, the reference data are stored in the battery memory and said processor is configured to read the reference data from the battery memory.

27. A module for use with a battery charger, said module including:
a shell defining a socket for receiving a battery;
a securement mechanism attached to said shell, said securement mechanism configured to releasably fit said shell to the battery charger;
a plurality of conductive members attached to said shell for establishing a conductive path between the battery charger and the battery over which a charging current is applied to the battery; and over which the voltage across the battery can be measured; and
a memory unit secured to said shell; said memory unit storing reference data readable by the battery charger from which, for a given voltage-at-load of the battery, and a given temperature the stored energy of the battery can be determined.

28. The module of claim 27, wherein the reference data in the memory unit provides information includes: a first set of data from which, for a given battery temperature and a given measured voltage-at-load, an adjusted voltage-at-load can be determined; and a second set of data from which, from the adjusted voltage-at-load, the stored energy of the battery can be determined.

29. The module of claim 27, further including a load resistor in said shell and a switch in said shell for selectively connecting the battery across said load resistor.

30. A rechargeable battery pack comprising:

a housing;

at least one rechargeable cell disposed in said housing;

a first set of terminals attached to said housing that are attached to said at least one rechargeable cell, wherein energy is applied to said at least one rechargeable cell through said first set of terminals and current is drawn from said at least one rechargeable cell through said first set of terminals;

a temperature sensor disposed in said housing from providing a signal representative of the temperature of said battery;

a memory disposed in said housing, said memory containing reference data readable by a processor from which, for a given voltage-at-load of said at least one rechargeable cell and for a given battery temperature, the energy stored in said at least one rechargeable cell can be determined; and a second set of terminals attached to said housing and connected to said memory wherein the reference data in the memory are read through said second set of terminals.

31. The battery of claim 30, wherein, the reference data in said memory includes: a first set of data from which, for a given battery temperature and measured voltage-at-load, an adjusted voltage-at-load can be determined; and a second set of data from which, for the adjusted voltage-at-load, the stored energy of the battery can be determined.

32. The battery of claim 30, wherein said battery further includes a data field in which data indicting the number of times the battery has been charged are stored.

33. The battery of claim 30, wherein said battery further includes a plurality of data storage fields in which data representative of the energy stored in the battery after charging are stored.

34. The battery of claim 30, wherein one of said first data terminals functions as a ground terminal for signals exchanged over said second set of data terminals.

* * * * *